(12) United States Patent
Early et al.

(10) Patent No.: US 11,446,061 B2
(45) Date of Patent: Sep. 20, 2022

(54) IMPLANTS AND METHODS FOR TREATING CHARCOT FOOT AND OTHER CONDITIONS

(71) Applicant: BESPA GLOBAL, LLC, Cedar Grove, NJ (US)

(72) Inventors: John Early, Dallas, TX (US); Gregory Pomeroy, Gorham, ME (US)

(73) Assignee: BESPA GLOBAL, LLC, Cedar Grove, NJ (US)

( * ) Notice: Subject to any disclaimer, the term of this patent is extended or adjusted under 35 U.S.C. 154(b) by 0 days.

(21) Appl. No.: 16/963,775

(22) PCT Filed: Feb. 1, 2019

(86) PCT No.: PCT/US2019/016257
§ 371 (c)(1),
(2) Date: Jul. 21, 2020

(87) PCT Pub. No.: WO2019/152784
PCT Pub. Date: Aug. 8, 2019

(65) Prior Publication Data
US 2021/0038261 A1    Feb. 11, 2021

Related U.S. Application Data

(60) Provisional application No. 62/626,324, filed on Feb. 5, 2018.

(51) Int. Cl.
*A61B 17/64*    (2006.01)
(52) U.S. Cl.
CPC ........ *A61B 17/645* (2013.01); *A61B 17/6475* (2013.01)

(58) Field of Classification Search
CPC ................... A61B 17/56; A61B 17/62; A61B 17/64–6491; A61B 17/66; A61B 17/68;
(Continued)

(56) References Cited

U.S. PATENT DOCUMENTS 10,226,292 B2 * 3/2019 Lundquist .......... A61B 17/7291
10,413,328 B1 * 9/2019 Klein, Jr. ............... A61B 17/62
(Continued)

FOREIGN PATENT DOCUMENTS

WO         96/35387 A1    11/1996
WO      2014062205 A1     4/2014
(Continued)

OTHER PUBLICATIONS

International Application No. PCT/US2019/016257, International Search Report and Written Opinion dated Apr. 19, 2019, 9 pages.
(Continued)

*Primary Examiner* — Eduardo C Robert
*Assistant Examiner* — Michelle C Eckman
(74) *Attorney, Agent, or Firm* — Corner Counsel

(57) ABSTRACT

A fixation system for immobilizing a skeletal structure is provided. It includes an internal fixation system having a rod-plate subsystem, a shaft subsystem, and a midfoot plate subsystem. It further includes an external fixation system adapted to connect to the internal fixation system and having a sole that provides a weight-bearing platform underneath a patient's foot to enable a patient to walk with the fixation system.

15 Claims, 16 Drawing Sheets

(58) Field of Classification Search
CPC . A61B 17/72; A61B 17/7225; A61B 17/7233; A61B 17/7241; A61B 17/7291; A61B 2017/681; A61B 17/8061; A61B 17/809
See application file for complete search history.

(56) References Cited

U.S. PATENT DOCUMENTS

| | | | | |
|---|---|---|---|---|
| 10,779,867 | B2* | 9/2020 | Penzimer | A61B 17/8625 |
| 11,033,303 | B2* | 6/2021 | Steinlauf | A61B 17/7233 |
| 2007/0191749 | A1 | 8/2007 | Barberio | |
| 2009/0275944 | A1* | 11/2009 | Huebner | A61B 17/60 606/54 |
| 2010/0121325 | A1* | 5/2010 | Tyber | A61B 17/8061 606/62 |
| 2011/0245830 | A1* | 10/2011 | Zgonis | A61B 17/6441 606/57 |
| 2011/0251614 | A1* | 10/2011 | Piraino | A61B 17/68 606/62 |
| 2011/0306977 | A1 | 12/2011 | Michel et al. | |
| 2013/0158608 | A1* | 6/2013 | Viola | A61B 17/8061 606/289 |
| 2013/0172942 | A1* | 7/2013 | Lewis | A61B 17/8014 606/281 |
| 2013/0204248 | A1* | 8/2013 | Singh | A61H 3/00 606/56 |
| 2016/0256194 | A1* | 9/2016 | Wong | A61B 17/62 |
| 2018/0310962 | A1* | 11/2018 | Ottoboni | A61B 17/6425 |
| 2019/0175236 | A1* | 6/2019 | Blacklidge | A61B 17/1682 |

FOREIGN PATENT DOCUMENTS

| | | | | |
|---|---|---|---|---|
| WO | WO-2014062205 A1 * | 4/2014 | | A61B 17/7225 |
| WO | 2017/083033 A1 | 5/2017 | | |
| WO | 2017083033 A1 | 5/2017 | | |

OTHER PUBLICATIONS

Capobianco CM, et al., "Charcot Foot Reconstruction with Combined Internal and External Fixation Case Report" Journal of Orthopaedic Surgery and Research, 2010, vol. 5, No. 7, pp. 1-9.

* cited by examiner

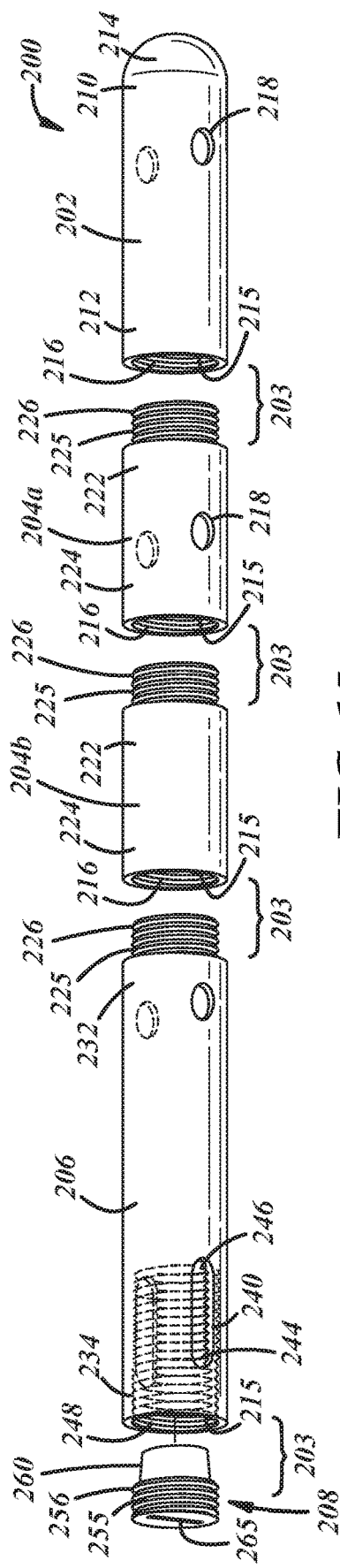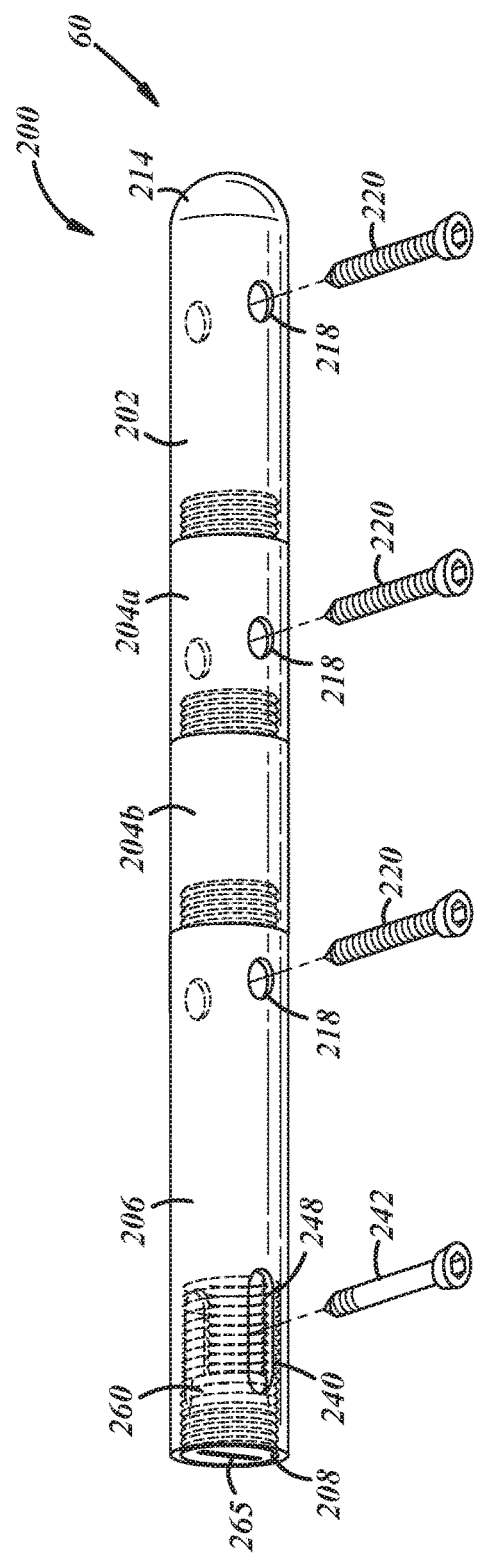
FIG. 15
FIG. 16

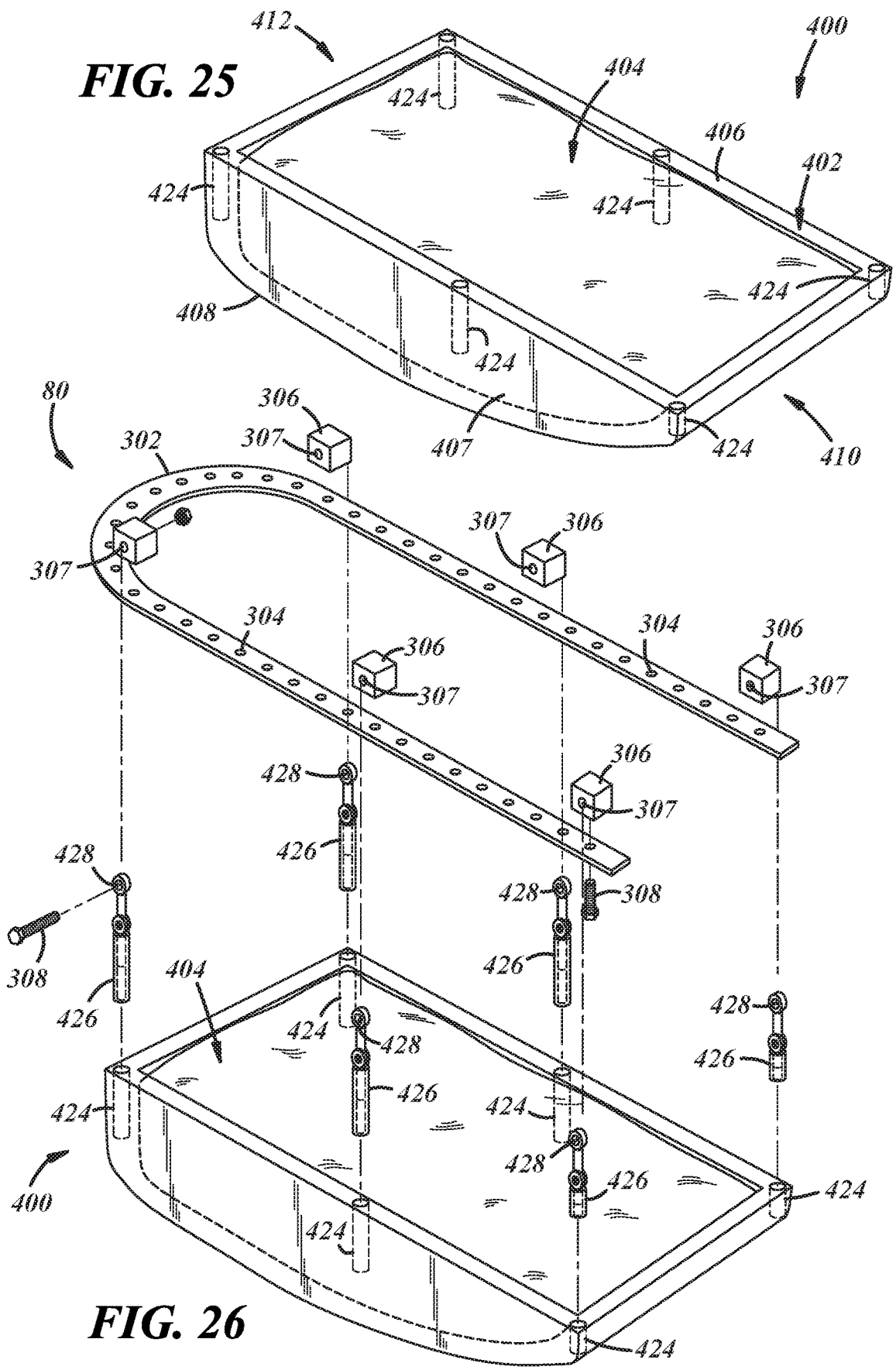

IMPLANTS AND METHODS FOR TREATING CHARCOT FOOT AND OTHER CONDITIONS

CROSS REFERENCE TO RELATED APPLICATIONS

The present application is a national phase filing under 35 U.S.C. § 371 of International Patent Application No. PCT/US219/016257 filed on Feb. 1, 2019, which claims the benefit of U.S. Provisional Application Ser. No. 62/626,324, filed Feb. 5, 2018, the disclosure of which is expressly incorporated herein by reference in its entirety.

TECHNICAL FIELD

The present invention relates to implants and methods for the treatment of various medical conditions typically involving mammalian extremities. One such condition is a human extremity deformity known as Charcot foot.

BACKGROUND

The terminology and descriptions contained herein are principally within the art field of, and for those skilled in the art of, orthopedic medicine. As such, only brief explanations of known subject matter within this art field will be provided because the details will be well known to those skilled in this art. The present invention, however, will be thoroughly described.

Damage or dysfunction of peripheral nerves of the foot causing numbness or weakness, also known as neuropathy, can lead to a condition known as Charcot arthropathy, or more commonly referred to as Charcot foot. More specifically, when a patient with neuropathy has an injury to their foot, the neuropathy may prevent them from sensing the injury. Without this defense mechanism which would otherwise cause the patient to feel pain, avoid continued injury and/or seek medical attention, the patient will continue to walk on the injured foot. This typically exacerbates the injury and affects surrounding areas of the foot, ultimately leading to possible deformity, disability, and even amputation of the foot in extreme cases.

One common symptom of advanced Charcot foot is the collapse of certain joints in the foot and a resulting disfigurement of the foot. Surgical treatment often involves the re-alignment and fixation of various bones within the foot to correct such deformity.

Various general internal fixation systems involving screws, plates, bolts, nails, and the like, are known and available for use to correct Charcot foot deformities. Similarly, various general external fixation systems involving external frames, pins, wires, screws, and the like, are also known and available for use to correct Charcot foot deformities. Some of the challenges in the art are constructing a customized patient solution to Charcot foot that includes internal fixation interacting with external fixation, and providing a weight-bearing platform for the affected limb, enabling a patient to walk soon after surgical intervention. The present invention offers solutions to these challenges and contemplates various novel and non-obvious combinations of implant modularity, interaction between internal and external fixation systems, and a weight-bearing platform.

SUMMARY OF THE INVENTION

A fixation system is provided for immobilizing a skeletal structure, the fixation system having an internal fixation system with one or more of a rod-plate system and a shaft system, and an external fixation system. The rod-plate system includes a rod affixed to a plate, the rod being adapted to be positioned in a bone canal, and the plate being adapted to be positioned on bone near the bone canal. The shaft system includes a shaft with a longitudinal axis, a slot on the shaft oriented in the direction of the longitudinal axis, and a hole on the shaft oriented at an angle to the longitudinal axis, the shaft further adapted to be positioned in a bone canal and configured to move two bone segments that comprise the bone canal toward each other. The external fixation system comprises a frame connected to a sole, the sole having a bottom adapted to contact ground.

The external fixation system further includes a pin to connect the rod-plate system or the shaft system to the external fixation system when the rod-plate system or the shaft system is located in bone. Optionally, the rod-plate system may be connected to the shaft system when both systems are located in bone. The rod of the rod-plate system can be modularly comprised of multiple segments that are joinable by a connection. This connection can be a threaded connection or a Morse-taper connection. The plate of the rod-plate system includes a first side adapted to face bone, an opposite second side, a length, a width, a plate axis along the length, and a projection extending from the first side. This projection has an opening to communicate with the rod of the rod-plate system. This opening communicates with the rod via a threaded connection. The opening is cylindrical and has a longitudinal opening axis, where the opening is oriented such that the opening axis is at an angle to the plate axis. Finally, the shaft of the shaft system can be modularly comprised of multiple segments each joinable at a connection. The fixation system can also include a midfoot plate system attached to bone, where the midfoot plate system comprises a plate and fasteners to attach the plate to bone.

Another embodiment of the fixation system that is provided for immobilizing a skeletal structure comprises an internal fixation system having a rod-plate system, a shaft system and an external fixation system. The rod-plate system includes a rod affixed to a plate, the rod being adapted to be positioned in a bone canal, and the plate being adapted to be positioned on bone near the bone canal, where the plate further includes a first side adapted to face bone, an opposite second side, a length, a width, a plate axis along the length, and a projection extending from the first side. This projection has a cylindrical opening with a longitudinal opening axis, where the opening is oriented such that the opening axis is at an angle to the plate axis. The rod-plate system is connected to the shaft system with at least one fixation element when both systems are located in bone, and the external fixation system may also be connected to one of the rod-plate system or shaft system.

Another embodiment of a fixation system is provided for immobilizing a skeletal structure, this fixation system having an internal fixation system including one or more of a rod-plate system and a shaft system, and an external fixation system.

The rod-plate system includes a rod affixed to a plate, the rod being adapted to be positioned in a bone canal, and the plate being adapted to be positioned on bone near the bone canal. The shaft system includes a shaft with a longitudinal axis, a slot on the shaft oriented in the direction of the longitudinal axis, and a hole on the shaft oriented at an angle to the longitudinal axis. The shaft is further adapted to be positioned in a bone canal and configured to move at least two bone segments through which the bone canal passes, toward each other. The external fixation system includes a frame connected to a sole, the sole having a housing and a bottom adapted to contact ground, where the housing contains a liner. The liner also includes an inflatable bladder in a shell. The sole can be connected to the frame with adjustable struts. The rod of the rod-plate system is modularly comprised of multiple segments each joinable by a connection, where the connection is either a threaded connection, a Morse-taper connection, or other type of connection.

The external fixation system further includes at least one pin to connect the external fixation system to either the rod-plate system or shaft system, and a frame connected to a sole, where the sole has a bottom adapted to contact ground. The fixation system can also include a midfoot plate system attached to bone, the midfoot plate system comprising a plate and a fastener.

Other features of the present invention will become more apparent after a review of the Detailed Description and accompanying drawings.

BRIEF DESCRIPTION OF THE DRAWINGS

The foregoing features of the invention will be apparent from the following Detailed Description, taken in connection with the accompanying drawings, in which:

FIG. 15 is an exploded elevational view of a shaft component of the internal fixation system;

FIG. 16 is a partial exploded elevational view of the shaft component of FIG. 15 shown assembled, along with several fasteners used to attach the shaft component to bone;

FIG. 25 is a perspective view of a sole component that is part of the external fixation system; and FIG. 26 is an exploded perspective view of various components of the external fixation system, including the sole component forming the weight bearing platform.

DETAILED DESCRIPTION

For convenience and efficiency of explanation only, the following descriptions of various embodiments of the present invention will be provided with reference to a human foot. However, this part of the body is only meant to be exemplary, non-limiting, and facilitative of a straightforward explanation of the invention, since aspects of the present invention are also envisioned to apply to other skeletal structures.

Figure 1:
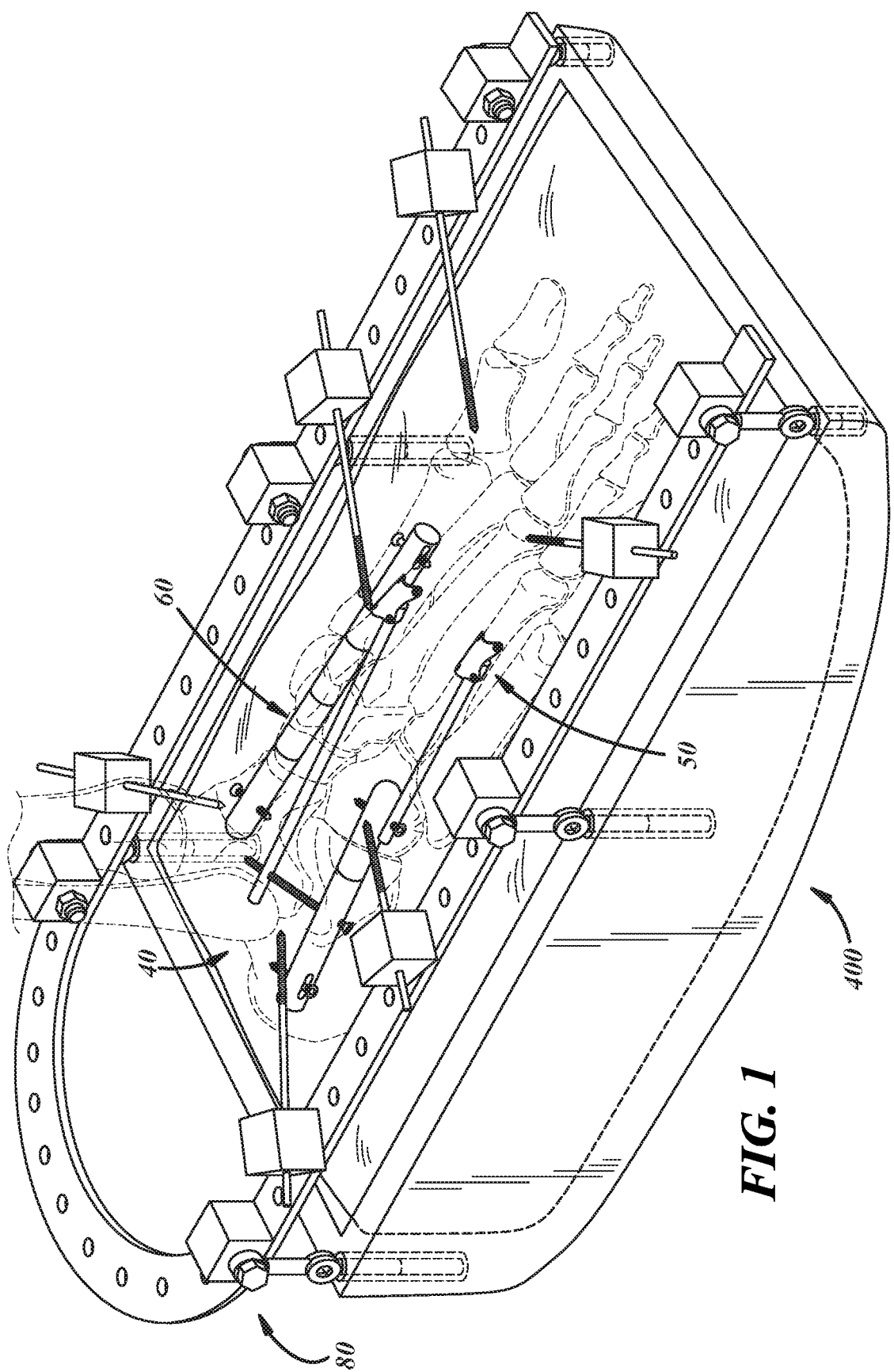
FIG. 1 is a perspective view of a fully assembled fixation system of a preferred embodiment of the present invention incorporating internal fixation, external fixation, and a weight bearing platform.

Referring to FIG. 1, a fixation system 10 for treating Charcot foot and other extremity deformities is depicted. Fixation system 10 comprises an internal fixation system 40 and an external fixation system 80. Internal fixation system 40 is comprised of three general subsystems referred to as rod-plate system 50, shaft system 60, and midfoot plate system 70. External fixation system 80 relevantly includes an optional weight-bearing platform, referred to as sole 400. The various systems, and certain of their various internal and external components, are modular, and may be mixed, matched and used together or independently, as will be discussed in more detail below.

Figure 1A:
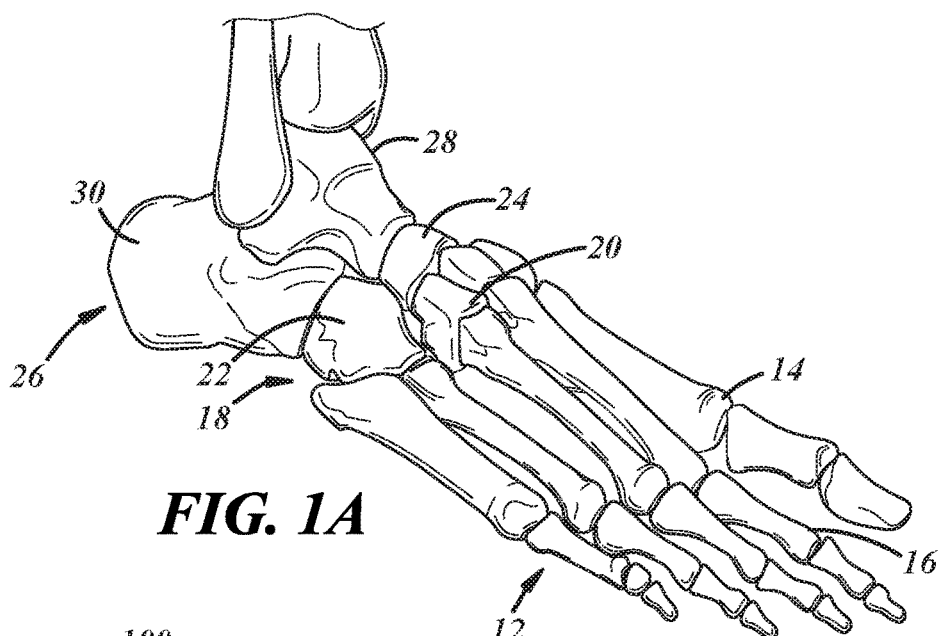
FIG. 1A is a perspective view of a human foot.

With reference to FIG. 1A, the human foot comprises the forefoot 12 which includes the metatarsals 14 and phalanges 16, the midfoot 18 which includes the three cuneiform bones 20, the cuboid 22 and the navicular bone 24, and the hindfoot 26 which includes the talus 28 and calcaneus 30. For the sake of conciseness, and because anatomy is well known to those skilled in the art, further reference to the various parts of the foot may be made herein without accompanying reference numbers.

Directional and spatial anatomical terminology that is also used herein is similarly well known to those skilled in the art. For instance, the term "medial" typically means closer to the midline of the body, and "lateral" typically means farther from the midline of the body. Further terms, such as "proximal", "distal", "anterior", "posterior", "superior", "inferior", and other such terms shall have their common and ordinary meanings in the art.

As used herein, the terms "rod" and "shaft" are chosen to describe the longitudinal members of the internal fixation system for convenience and efficiency of explanation only, and are not meant to be limiting. Thus, "rod" and "shaft" are intended to be non-limiting generic terms that may include such things as a bolt, nail, screw, strut, beam and the like.

Figure 20:
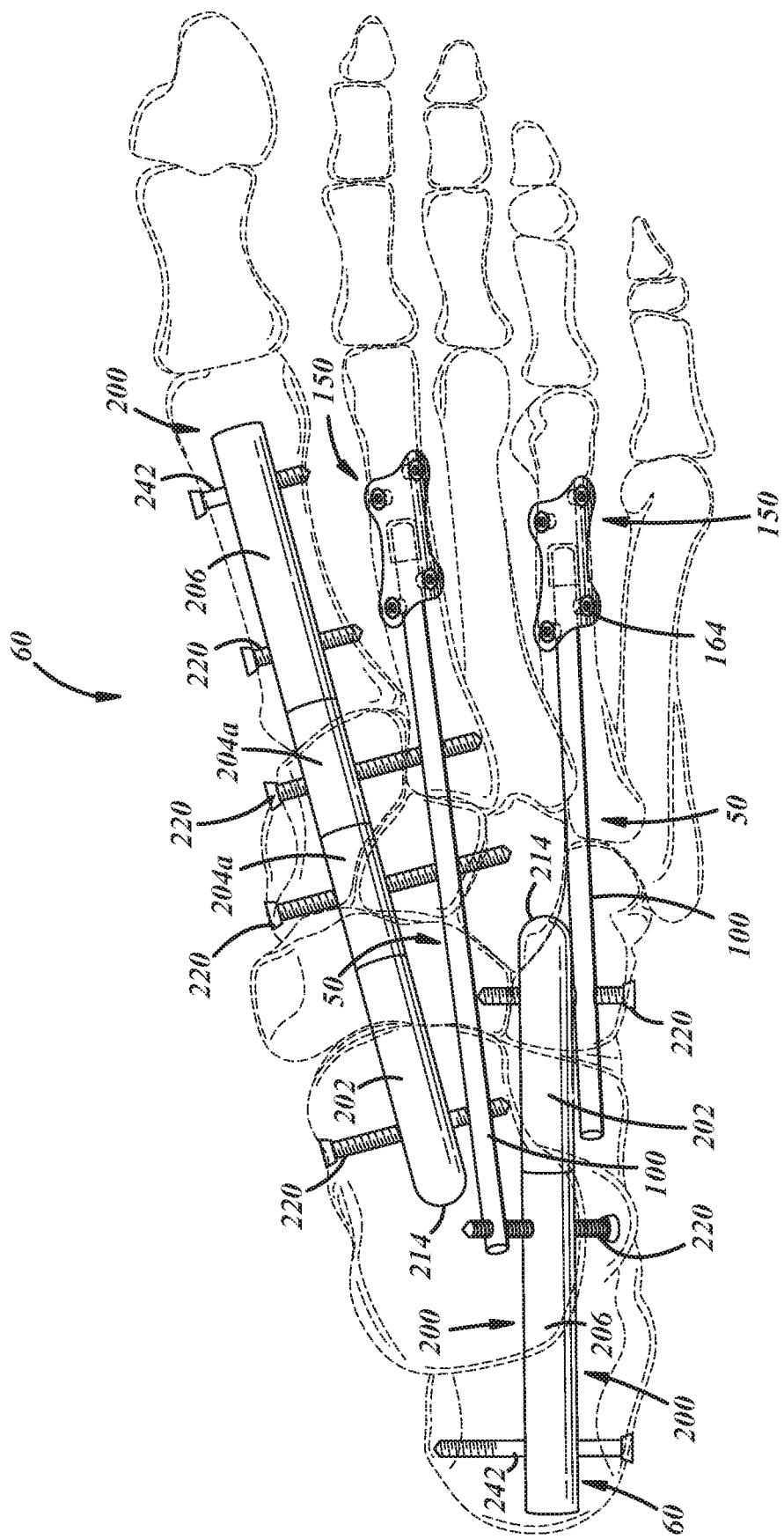
FIG. 20 is a top view of various internal fixation systems implanted in a foot, including plate-rod constructs, and rods connected to shafts.
Figure 21:
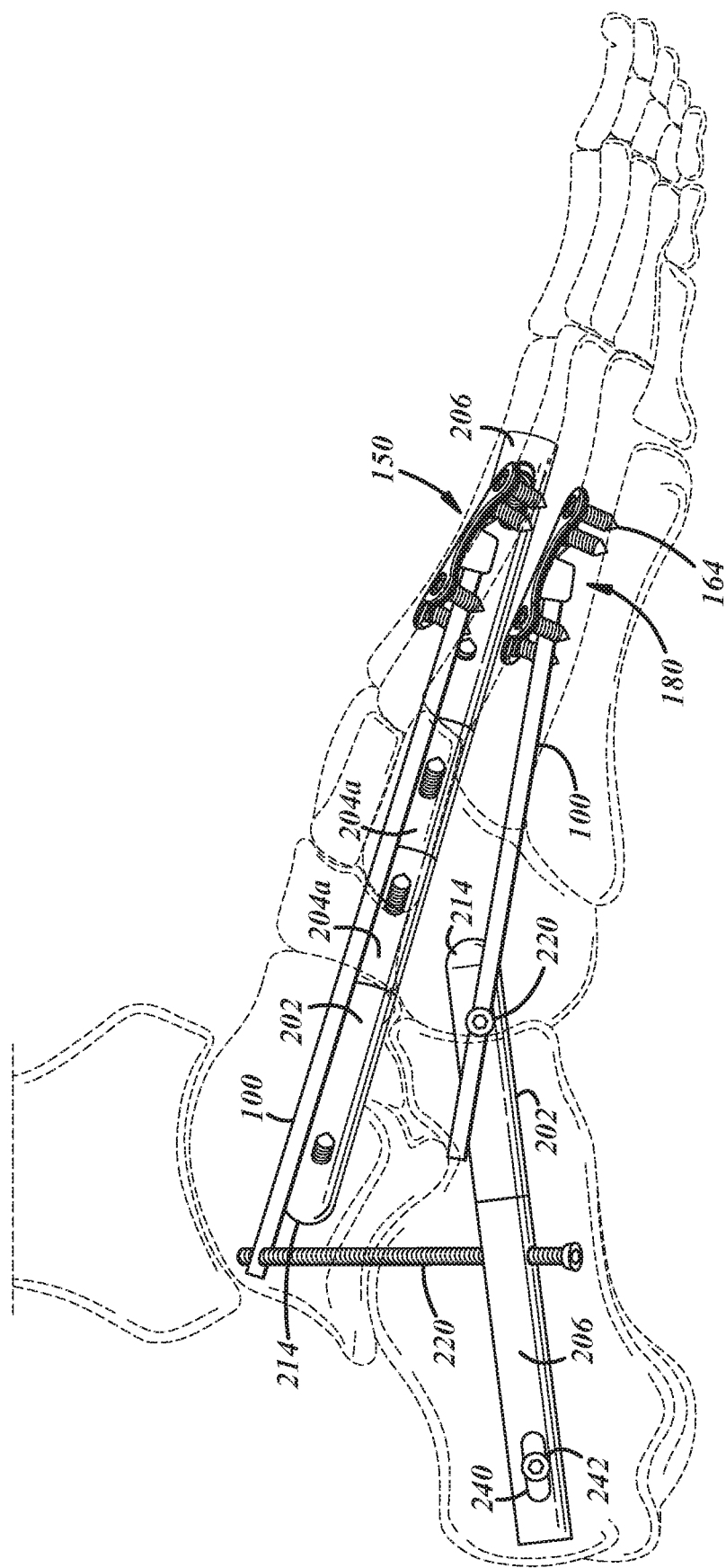
FIG. 21 is a side elevational view of what is shown in FIG. 20.
Figure 22:
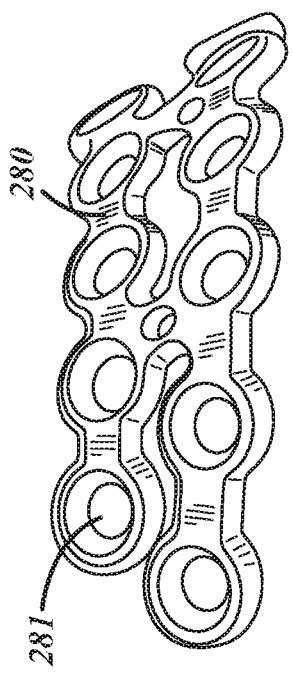
FIG. 22 is a perspective view of a midfoot plate component of the internal fixation system.
Figure 23:
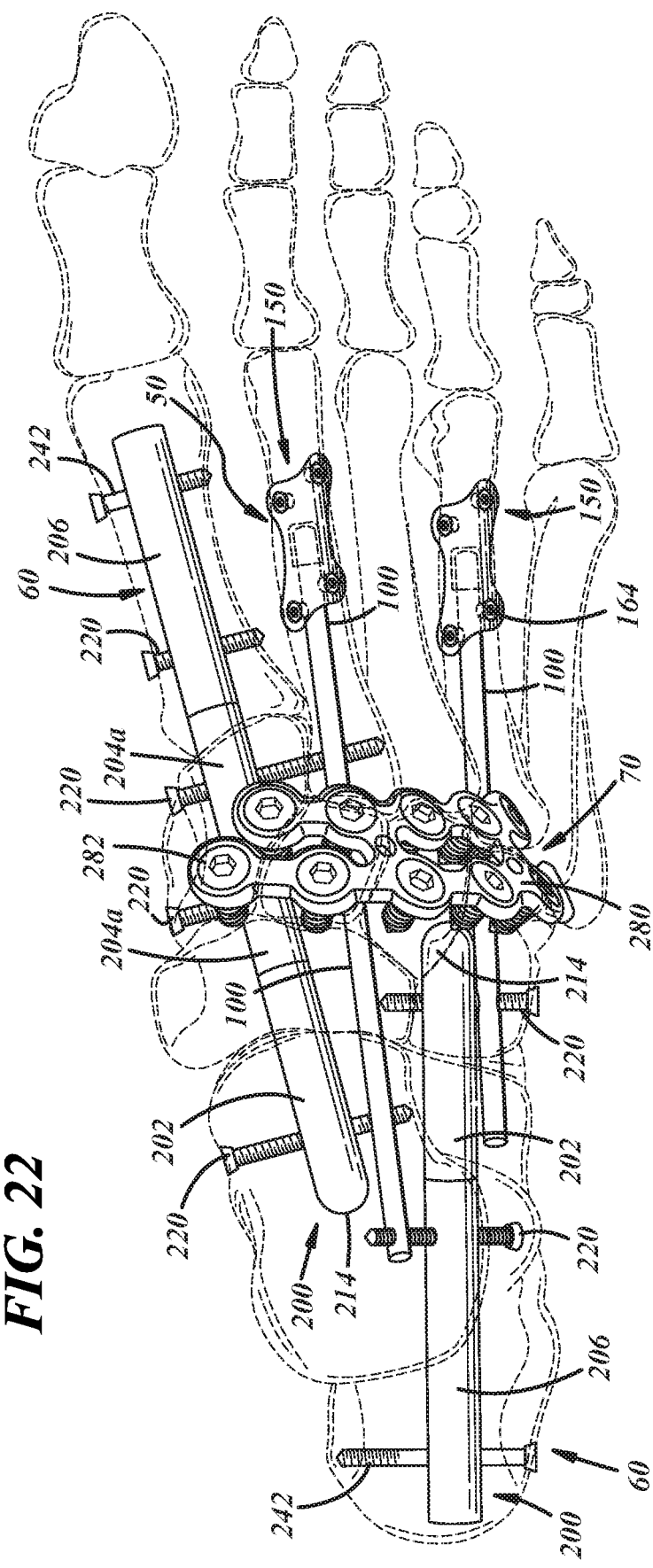
FIG. 23 is a top plan view of the midfoot plate component implanted in a foot along with the other internal fixation systems depicted in FIGS. 20 and 21.
Figure 24:
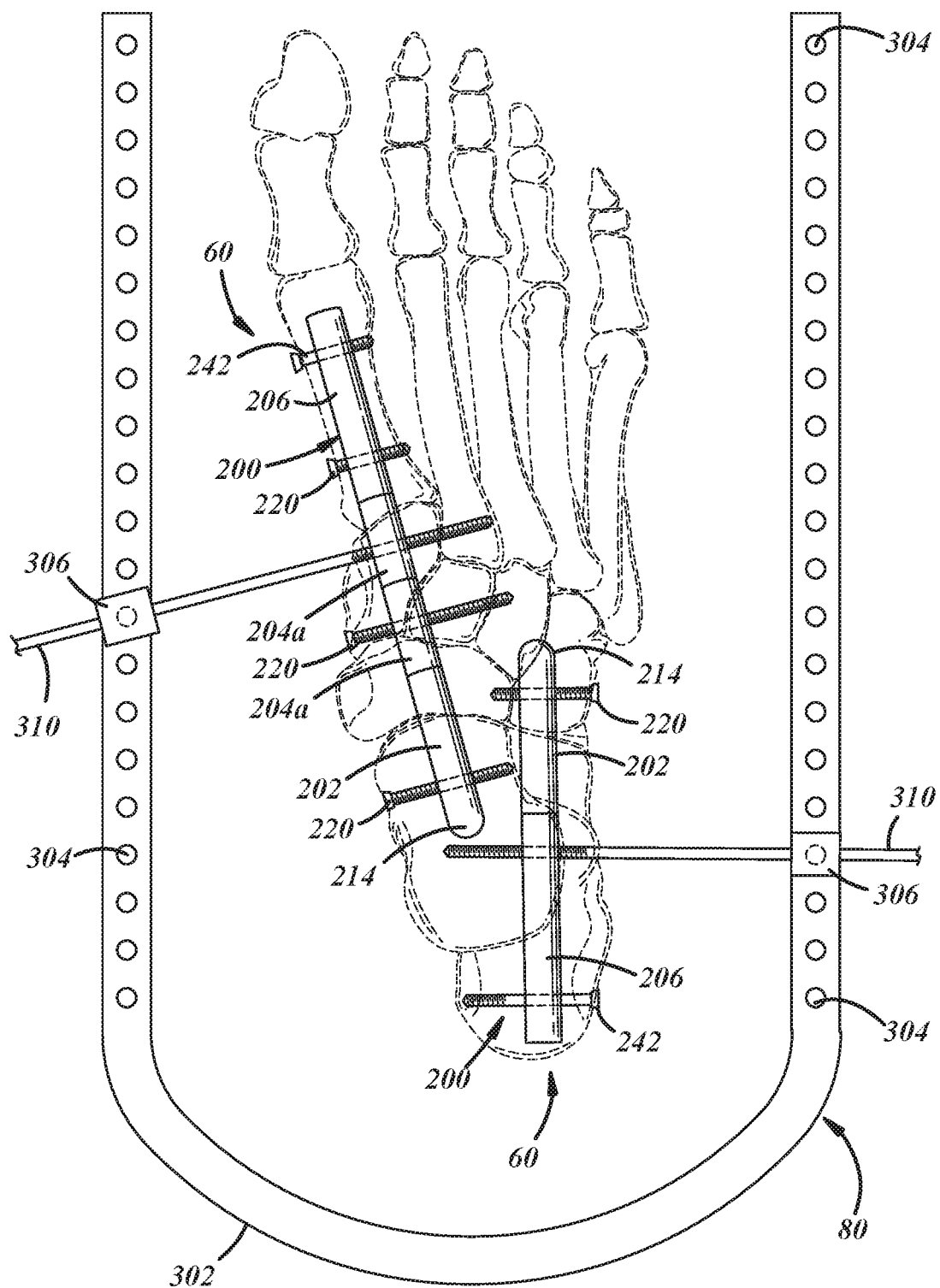
FIG. 24 is a top view of two shaft systems of the internal fixation system implanted in a foot and connected to an external fixation system.

As an overview, FIGS. 2-14 depict components of rod-plate system 50, which is one of three subsystems of internal fixation system 40. FIGS. 15-19 depict components of shaft system 60, which is the second of the three subsystems of internal fixation system 40. FIGS. 22-23 depict midfoot plate system 70, which is the third subsystem of internal fixation system 40. FIGS. 20, 21, and 23 depict various combinations of the various internal fixation subsystems. And FIGS. 24-26 depict components of the external fixation system 80.

With reference to FIGS. 2-5, rod 100 includes a body 108 with a first end 104 and a second end 106, which terminates at a flat surface 134. As alternatively depicted in FIG. 5, second end 106 may terminate at a rounded surface 136. As will be discussed later, rounded surface 136 is better suited to facilitating the insertion of rod 100 into a bone canal.

Rod 100 may be unitary and continuous from end 104 to end 106, or comprised of two or more joined segments, such as first segment 110 joined at connection 102 to second segment 112. Connection 102 generally represents various connection mechanisms that enable the joining of two rod segments together, and will be discussed in more detail, below.

Body 108 of rod 100 may have a generally circular transverse cross-sectional shape or may have any other cross-sectional shape such as oval, polygonal or otherwise, as may be suited for various applications. Body 108 may also be roughened, knurled, or otherwise provided with any other surface topography known in the art, for various purposes also known in the art, such as to provide an improved surface for bone adhesion. Furthermore, rod 100, or any of its segments, may be solid or hollow.

Figure 3:
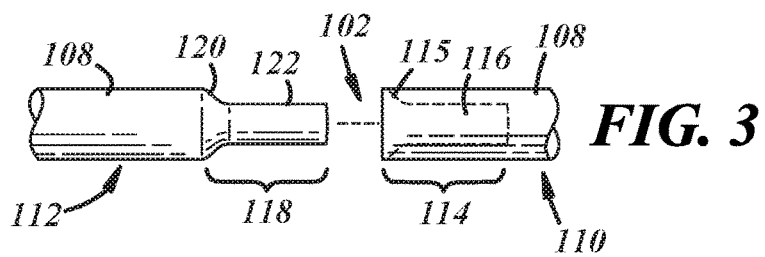
FIG. 3 is a side elevational view of an intrabody connection mechanism facilitating modularity of the rod component of the internal fixation system.
Figure 4:
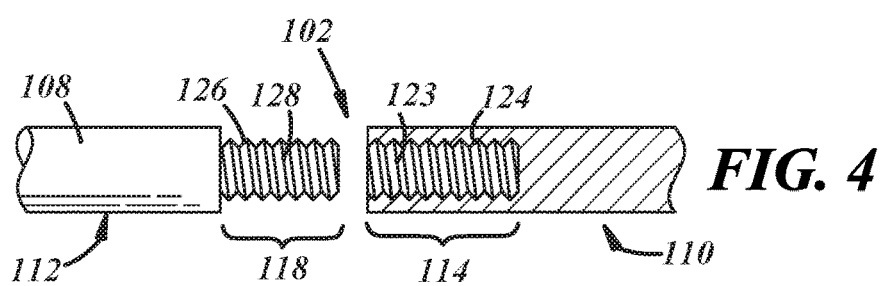
FIG. 4 is a side elevational view of an alternative connection mechanism to that shown in FIG. 3.

The first and second segments 110, 112 of rod 100 are joined together at connection 102. FIG. 3 depicts a Morse taper-type connection, and FIG. 4 depicts a threaded connection, both of which will be described in more detail, below. Of course, other alternative connections are envisioned. It is further envisioned that in the case of multiple segments of a rod, the same type of connection, or different types of connections, may be employed to join each two segments of a rod 100 together, depending on a wide array of factors, as known to those skilled in the art. Similarly, if it is desired to use more than one rod 100 in an implantation, it is envisioned that one segmented rod may be assembled with one type of connection and another segmented rod may be assembled with another type of connection. The rationale for doing so may be due to, for example, the various details and advantages of one type of connection over another, and the resultant properties of the assembled rods with the different connection types.

As mentioned above, FIG. 3 depicts a Morse-taper type of connection. Second rod segment 112 has a male end 118. Male end 118 includes a conical shoulder 120 that tapers to a projection 122 having a smaller diameter than body 108. First rod segment 110 has a female end 114 comprising a conical opening 115 significantly decreasing in diameter and leading to an inner bore 116. In general, female end 114 is dimensioned to matingly receive male end 118. Thus, shoulder 120 has a general correspondence and sizing relationship to opening 115, and similarly, projection 122 to bore 116. More specifically, as is known in the art of Morse tapers, one or both of male end 118's shoulder 120 and projection 122 have circumferential dimensions that are slightly larger than those of the corresponding female end 114's opening 115 and bore 116. When male end 118 is inserted into female end 114, the interference in dimensions results in a press-fit, locking second rod segment 112 to first rod segment 110.

If it is desired to not have a rotational preference to the axial alignment, or no keying effect, of first rod segment 110 to second rod segment 112, then the Morse-taper mating surfaces described just above would all have circular cross sections. Of course, if a keying effect would be desired, then the cross-sectional shapes of the mating surfaces may be oval, polygonal, or any other shape known in the art.

FIG. 4, as an alternative embodiment, depicts a threaded connection mechanism 102 between first rod segment 110 and second rod segment 112. Female end 114 of first rod segment 110 comprises a bore 123 with internal threads 124. Male end 118 of second rod segment 112 comprises a corresponding projection 126 with external threads 128. Projection 126 with external threads 128 is configured to be matingly received in a threaded fashion in threaded bore 123 of female end 114. When so assembled, first rod segment 110 is securely connected to second rod segment 112.

Figure 5:
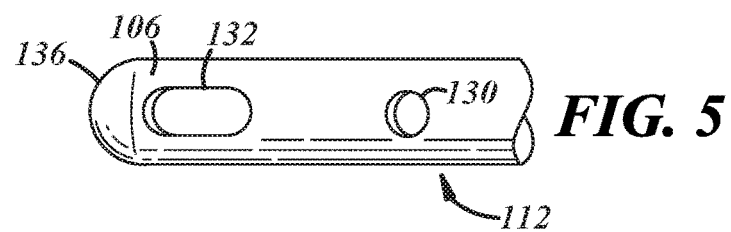
FIG. 5 is a side elevational view of an alternative end of the rod component.

With reference to FIG. 5, rod 100 may have one or more through-holes 130 configured to receive a fastener (not shown), such as a bone screw, or other fastener known in the art. As will be evident to those skilled in the art, through-hole 130 may be internally threaded so as to threadably receive a corresponding threaded fastener, or may be provided with any other connection mechanism known in the art. In other embodiments, through-hole 130 is smooth and does not contain any form of connection mechanism. Through-hole 130 can receive a fastener to facilitate fixation of rod 100 within the medullary canal within which rod 100 may be positioned. Alternatively, through-hole 130 may receive a fastener that is also connected to one or more other rods 100 which themselves may be positioned and fixed relative to other human bones in the foot to provide fixation across such bones. In yet other embodiments, hole 130 may receive fixation elements from external fixation system 80.

Slot 132 is depicted on second end 106 of rod 100, and its length is oriented generally along the long axis of rod 100. The purpose and function of slot 132 will be discussed in more detail with reference to FIGS. 15-17A, where shaft 200 has a relatively similar slot 240.

Figure 2:
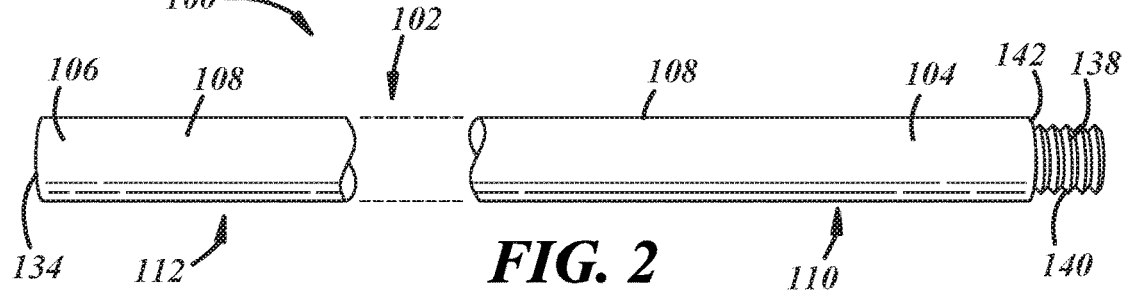
FIG. 2 is a side elevational view of a rod component of the internal fixation system shown in FIG. 1.

With reference to FIG. 2, first end 104 of rod 100 includes a projection 138 having external threads 140, and a shoulder 142. As will be described in more detail below, projection 138, external threads 140, and shoulder 142 communicate with connection plate 150 (FIG. 11) to form an improved fixation construct. In other embodiments, connection mechanisms other than threads are envisioned such as, for instance, interference fit, cross-screw (FIG. 12), nut-and-bolt, ratchet mechanism, and other connection methods known in the art.

In its contemplated embodiments, rod 100 may be formed of any suitable material known in the art, such as titanium, or other biocompatible materials having mechanical properties suitable for the contemplated uses of fixation system 10. Furthermore, rod 100 may be coated with any suitable biocompatible coating known in the art, such as hydroxyapatite or the like, or may be uncoated, as needed to suit particular mechanical and clinical needs.

In the contemplated embodiments of the present invention, rods 100 may be provided in various lengths and configured to provide axial stability to the bones in which they reside. In some embodiments, a rod 100 is configured to have a length such that the rod 100 extends from a portion of a metatarsal into the talus or calcaneus of the hindfoot to provide axial stability. Rods 100 may also be provided in various diameters such as, for instance, a diameter of about 3 mm, about 3.5 mm, about 4 mm, about 4.5 mm or any other diameter known in the art that is suitable for the intended use of rod 100. As will be evident to one skilled in the art, the selection of one or more appropriately sized rods 100 may be made by the surgeon in the operating room during surgery, or the rods 100 may be selected and prepared prior to surgery.

FIGS. 6-12 depict embodiments of a connection plate component 150 that are configured to facilitate connection between a rod, such as rod 100, and a bone, to improve the robustness and rigidity of an internal fixation construct of fixation system 10. As described in an exemplary embodiment herein, plate 150 attaches to a metatarsal of a human foot. However, the description of plate 150 in the exemplary embodiment is presented for convenience and efficiency of explanation only, and is not meant to be taken as limiting the scope of the invention to the exemplary embodiment. In other embodiments, plate 150 may be fixed to bones other than the metatarsal of a human foot. For instance, plate 150 may be fixed to a metacarpal bone of a human hand or to another human bone. Plate 150 may be generally parallelogram, square, rectangular, oval, or any other shape known in the art that is suitable for fixation to the bone to which plate 150 is to be affixed.

Referring to FIGS. 6-12, plate 150 includes a first side 152, a second side 154 opposite first side 152, a thickness T extending therebetween, and a perimeter edge 156. In an embodiment, plate 150 includes four lobes 158 each having a lobe edge 160 adjacent lobe 158 and an aperture 162 that extends through the thickness T of the plate 150. In other embodiments, plate 150 may have more or fewer lobes 158, while in still other embodiments, plate 150 may have four lobes, wherein lobes 158 includes more or fewer apertures 162. Apertures 162 are configured to receive fasteners, such as screws 164, and are generally circular in shape, however other shapes for one or more apertures 162 may be used, such as slots, for example. Apertures 162 include a first flared portion 166 on first side 152 of plate 150 and a second flared portion 168 on second side 154 of plate 150. As will be understood by those skilled in the art, second flared portions 168 are configured to receive a fastener head therein so that the fastener head may be partially or fully recessed within plate 150. Additionally, the combination of flared portions 166, 168 together, enables for angular placement of a fixation element, such as screw 164, through plate 150. In various embodiments, the flared portions 166, 168 include a gradual taper or conical shape, a recessed or step-down area, or a curved or rounded portion, or any other flare known in the art to receive the head of a fastener. In other embodiments, the flared portions 166, 168 may be omitted so that apertures 162 extend perpendicular to thickness T. In such embodiments, fasteners without protruding heads can be used. Additionally, it is envisioned that the one or more apertures 162 may be designed to accommodate a snap ring (not shown) or other mechanism to prevent a screw 164 from backing out of plate 150. Such back-out mechanisms are well known in the art.

Figure 6:
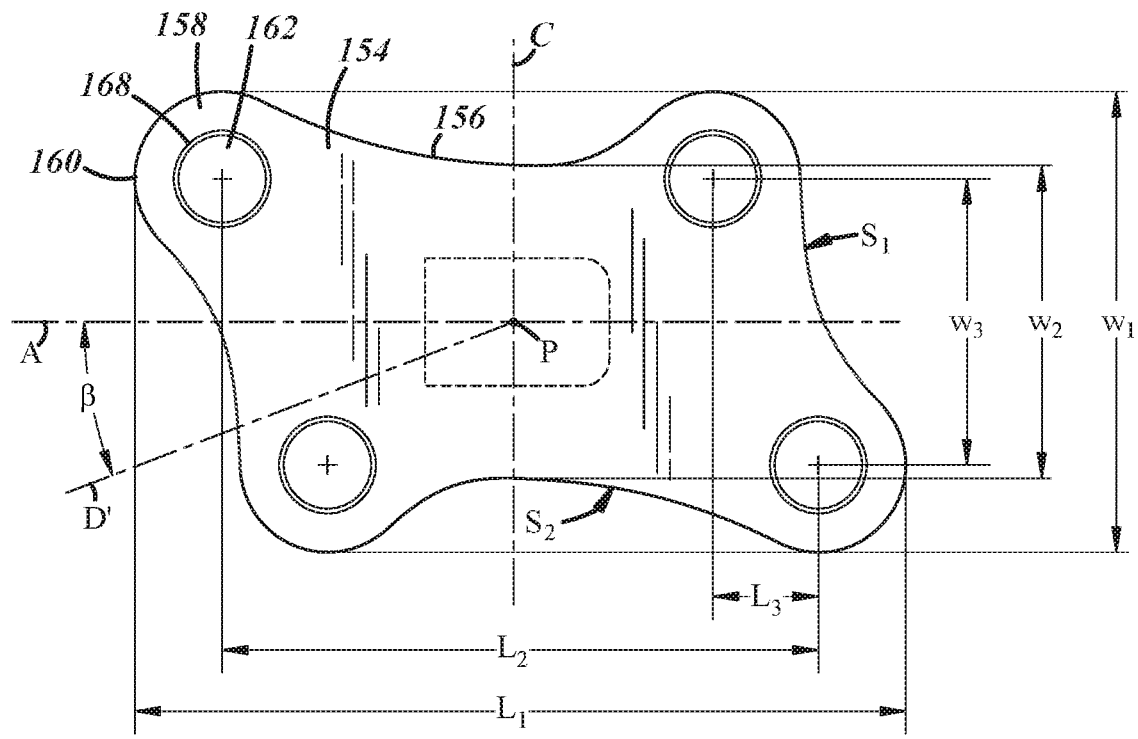
FIG. 6 is a top view of a connection plate component of the internal fixation system shown in FIG. 1.

Referring to FIG. 6, embodiments of plate 150 may be of various shapes and configurations. Plate 150 includes a long axis A, a short axis C, a length L1 measured as the largest length along the long axis A, and a width W1 measured as the largest width along the short axis C. The shape of the exemplary plate 150 is generally a parallelogram, however the shape and configuration of plate 150 can be varied. For instance, reducing the length L1 or increasing the width W1 would result in a parallelogram shape that is shaped more like a square. In other embodiments, length L1 can be increased and width W1 can be reduced resulting in a rectangularly shaped parallelogram having one pair of opposing sides of perimeter edge 156 longer than the other pair.

The length L2 is the shortest distance between opposing sections of perimeter wall 156 at the intersection of the long axis A and the perimeter wall 156, and width W2 is the shortest distance between opposing perimeter walls 156 at the intersection of the short axis C and the perimeter wall 156. As depicted in FIG. 6, in an embodiment, the length L2 and width W2 cooperate to provide a generally parallelogram shape. In some embodiments, the length L2 can be increased or reduced to provide a shape that is more rectangular or more square, respectively. In other embodiments, the width W2 can be increased or reduced to provide a shape that is more square or more rectangular, respectively.

The location of the lobes 158 can also be varied. Length L3 is the length between the center of two apertures 162 which are both located on the same side of the short axis C, and width W3 is the width between the same apertures 162. In some embodiments, length L3 can be increased to create a shape that is more diamond-like. In other embodiments, length L3 can be reduced, which results in a shape that is less like a parallelogram. In some embodiments, length L3 can be reduced to zero such that the two apertures 162 are axially aligned along the short axis C, that is, both apertures 162 are the same distance from the short axis C. In some embodiments, the width W3 can be increased to create a shape that is more like a square. In other embodiments, width W3 can be reduced, which results in a shape that is more like a rectangle.

The location of each aperture 162 within its lobe 158 relative to the lobe edge 160 can also be modified. In some embodiments, each aperture 162 can be disposed closer to its respective lobe edge 160, while in other embodiments, each aperture 162 can be disposed farther from its respective lobe edge 160. In still other embodiments, the positions of the apertures relative to their respective lobe edges 160 may be mixed and matched, as may be desirable based on a variety of factors, such as for example, if plate 150 is made as a custom patient-matched implant that necessitates an altered configuration.

With reference to FIG. 6, S1 is the shape of the periphery of plate 150 along the C axis. S2 is the shape of the periphery of plate 150 along the A axis. These shapes S1, S2, are depicted as concavities on the periphery of plate 150. S1, S2 may be complexly formed splines created from transitions of radii of different lengths, or shaped in any other way known in the art, including having no curvature and being straight. In some embodiments, the concavities of S1 and S2 may be grossly exaggerated toward the center of the plate 150, thus resulting in there being less plate 150 material. In other embodiments, one or both of shapes S1 and S2 may be convexities.

As will be evident to those skilled in the art, there are a myriad of possible configurations of plate 150. This further facilitates the customizability of plate 150. For instance, plate 150 may be provided with greater or lesser L3 and W3 dimensions so as to provide more or less distance, respectively, between the apertures 162. Similarly, others of the foregoing dimensions may be arranged to provide an altered plate 150 according to the surgeon's preference or the particular patient's needs. In some embodiments, various dimensions may be modified together to alter various aspects of plate 150, such as the locations of lobes 158 relative to perimeter edge 156.

For the foregoing description, it should be understood that, while various lengths and widths were depicted on only one side of axis A or C in FIG. 6, such depiction was made for clarity and efficiency of explanation only, and is not meant to be limiting. As such, for any particular length or width described, the same aspects and dimensions on the opposite side of axis A or C exist and can be modified as described above. It should further be understood that the foregoing dimensions do not need to be symmetrical and can be varied from one side of axis A or C relative to the other side of axis A or C, respectively.

Figure 9:
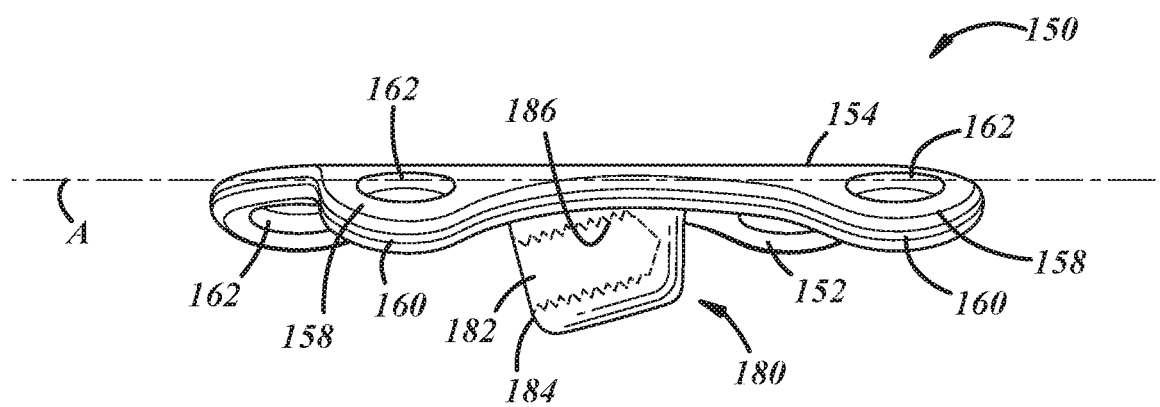
FIG. 9 is a side elevational view of the connection plate component shown in FIG. 8.
Figure 10:
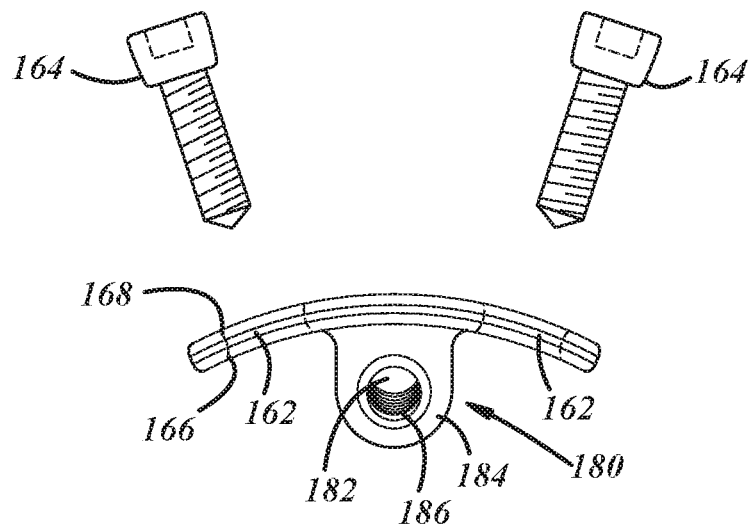
FIG. 10 is a front exploded view of the connection plate component shown in FIG. 8 with several fasteners to be used to attach the plate component to bone.

Continuing to refer to FIGS. 6-12, plate 150 may include a projection 180 that extends generally orthogonally away from first side 152 of plate 150. The purpose of projection 180 is to enable plate 150 to be connected to a rod 100. Projection 180 includes an inner opening 182 which may be configured to receive a first end 104 or second end 106 of the rod 100 of FIGS. 2-4, and also includes an external face 184 (FIG. 10). In an embodiment, inner opening 182 may be formed with internal threads 186 to communicate with external threads 140 of projection 138 of rod 100 (see FIGS. 2 and 11). In some embodiments, inner opening 182 is a blind bore (see, for instance, FIGS. 7 and 9), while in other embodiments, inner opening 182 may extend completely through projection 180. In still other embodiments, inner opening 182 may be unthreaded, and the connection between opening 182 and rod 100 may be a Morse-taper type connection.

Figure 11:
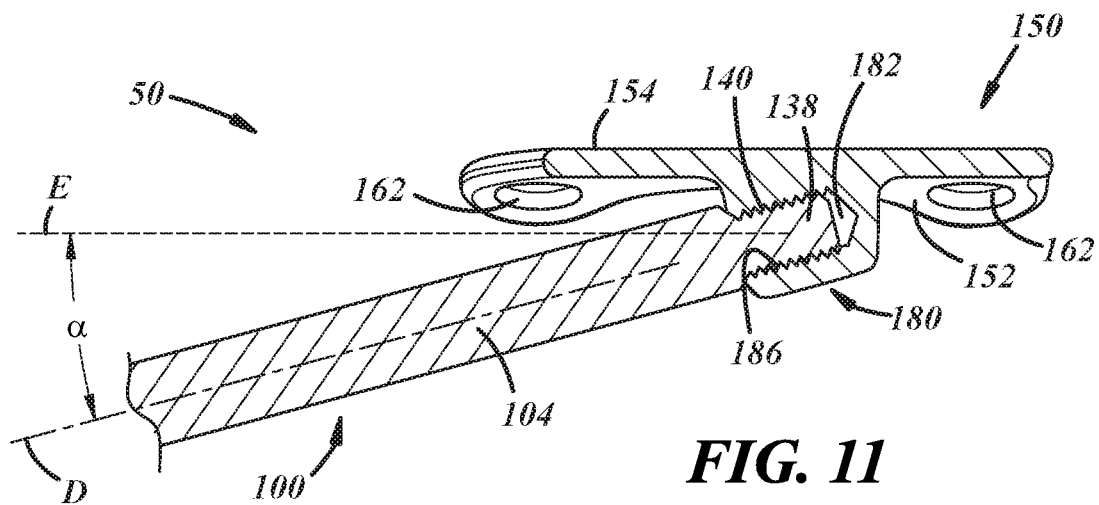
FIG. 11 is a cross-sectional view of the connection plate component shown in FIG. 8 taken along section line 11-11, connected with the rod component of FIG. 2, which is also shown in cross-section for consistency.

With reference to FIGS. 2 and 11, as will be evident to those skilled in the art, during assembly of rod 100 to plate 150, as rod 100 is inserted into opening 182 to a sufficient depth, the shoulder 142 of rod 100 will contact face 184 of projection 180 of plate 150, thereby halting the movement of rod 100 into projection 180 and ensuring that rod 100 does not pass beyond projection 180.

In still other embodiments, plate 150 and, optionally, rod 100 may be configured with other structures or mechanisms known in the art that facilitate connection of plate 150 to a rod 100.

Figure 12:
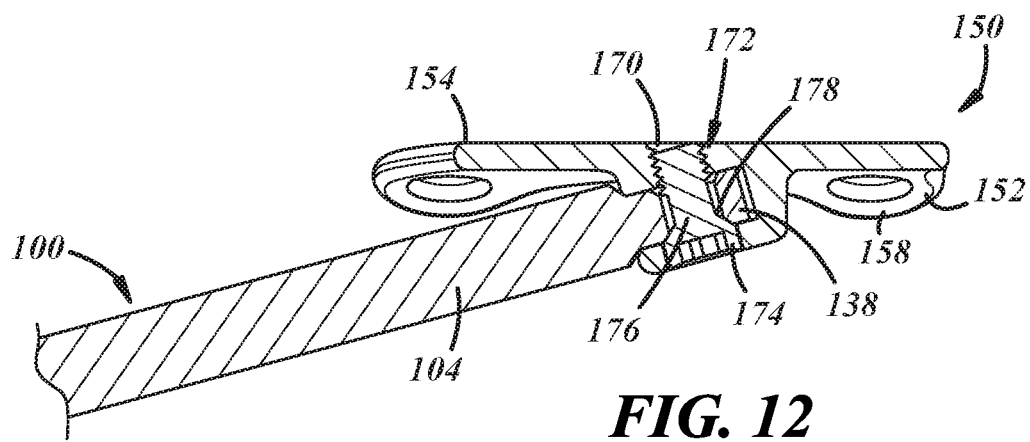
FIG. 12 is a cross-sectional view similar to that of FIG. 11, but depicting an alternative connection of the rod component to the plate component.

Referring to the exemplary embodiment of FIG. 12, rod 100 does not have threads 140 on its projection 138 but has a through-hole 178 passing transversely through projection 138. Plate 150 is provided with a partially threaded transverse hole 170 having threads proximal to second side 154 of plate 150. Transverse hole 170 is configured to receive a partially threaded screw 176 and threadably communicate with screw 176 in the region shown as 172. After rod 100 is inserted into opening 182 of projection 180, rod 100's through-hole 178 is axially aligned with transverse hole 170. Optionally, this alignment may be further facilitated by having cooperating keyed surfaces on projection 138 and opening 182, as is known in the art. Then, screw 176 is inserted into hole 170 and through rod 100's through-hole 178, and threadably fixed to plate 150 at region 172. A portion of hole 170 may be countersunk, or otherwise formed, to accept in whole or in part, a head of a fastener, such as head 174 of screw 176, to enable head 174 to be countersunk into the projection 180 of plate 150.

Figure 7:
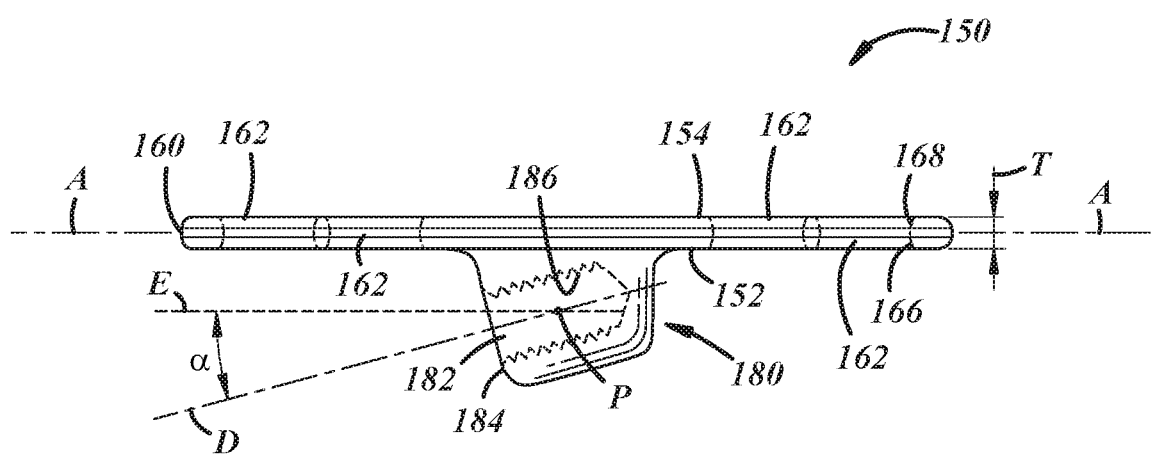
FIG. 7 is a side elevational view of the connection plate component.
Figure 8:
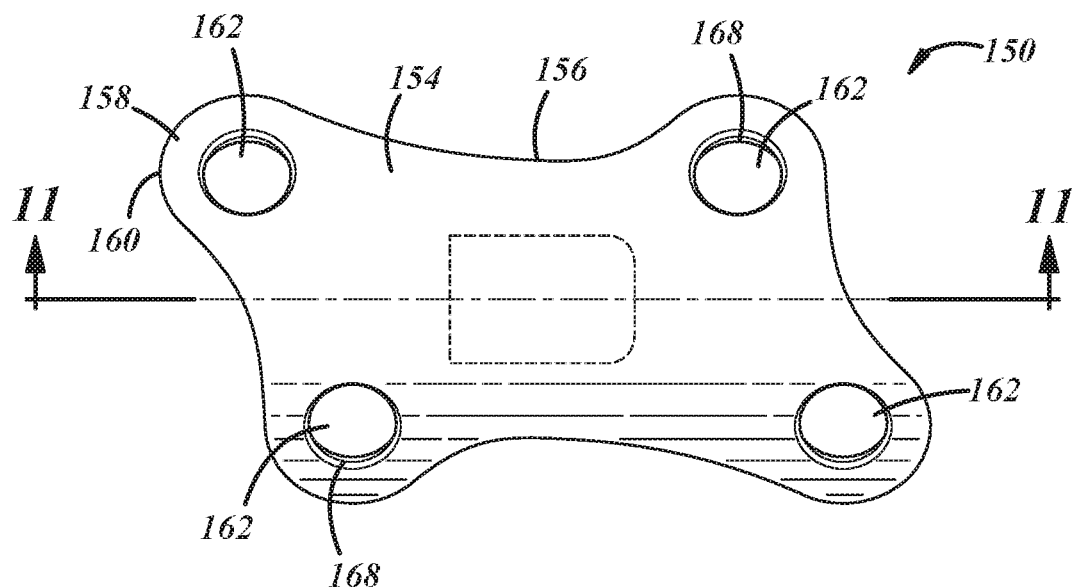
FIG. 8 is a top view of an alternate embodiment of the connection plate component.

Referring to FIGS. 6-8 and 11, opening 182 in projection 180 of plate 150 is formed around longitudinal axis D (FIG. 7). In this embodiment, axis D is in the same plane as axis A, which plane is defined by the cross-section line 11-11. Axis D travels through point P which is a point in space within opening 182. Line E is a reference line drawn parallel to axis A of plate 150, and offset from axis A by virtue of also traveling through point P. As better seen in FIG. 11 where rod 100 is assembled with plate 150, angle α, which is the angle between axis D and line E, represents the angle between rod 100 and plate 150. Angle α may range anywhere from about 5° to about 30° with reference to line E, or may be any other angle that may suit various clinical needs, as is evident to those skilled in the art. In an alternate embodiment (not shown), angle α may even be a negative angle, and in such case, plate 150 would be shaped to accommodate rod 100 projecting through and above its second side 154. For example, plate 150 may have an opening through its thickness T to accommodate rod 100, or perimeter edge 156 of plate 150 may be concavely shaped so as to make room for rod 100 to pass adjacent to plate 150.

In other alternative embodiments, the orientation of rod 100 to plate 150 may be different. For example, axis D may be oriented at an angle to the plane formed by cross-section line 11-11. This is depicted in FIG. 6 with reference to axis D'. Axis D' is depicted at angle β relative to axis A. Angle β, like angle α, represents the angle of rod 100 to plate 150 when they are assembled together. Of course, many other alternative configurations are envisioned.

It is further envisioned that to accomplish the angulation of rod 100 to plate 150, opening 182 in projection 180 may be designed at different angles as discussed above. Or as will be apparent to those skilled in the art, projection 180, itself, may be designed on plate 150 at different angles and configurations.

Optionally, plate 150 may be flat, as in FIG. 7 for example, or curved, as in FIG. 9. The curvature of plate 150 in FIG. 9 is along long axis A. However, as will be readily apparent to those skilled in the art, many other curves and shapes of plate 150 are possible, as dictated by different considerations such as manufacturability, or various clinical factors such as anatomical configurations of specific patients. Furthermore, it is contemplated that plate 150 may be provided as a rigid, non-bendable plate, or alternatively, as a deformable plate, enabling intra-operative bending, as needed.

Plate 150 may be formed of any one or more suitable biocompatible materials known in the art, such as titanium, PEEK or other biocompatible materials having mechanical properties suitable for the contemplated uses of plate 150. Plate 150 may also be coated in whole, or in part, with any suitable biocompatible material coating known in the art.

For ease of reference, when rod 100 is assembled with plate 150, this may also be referred to as a rod-plate construct, and so the rod-plate system 50 may be comprised of one or more rod-plate constructs.

Figure 13:
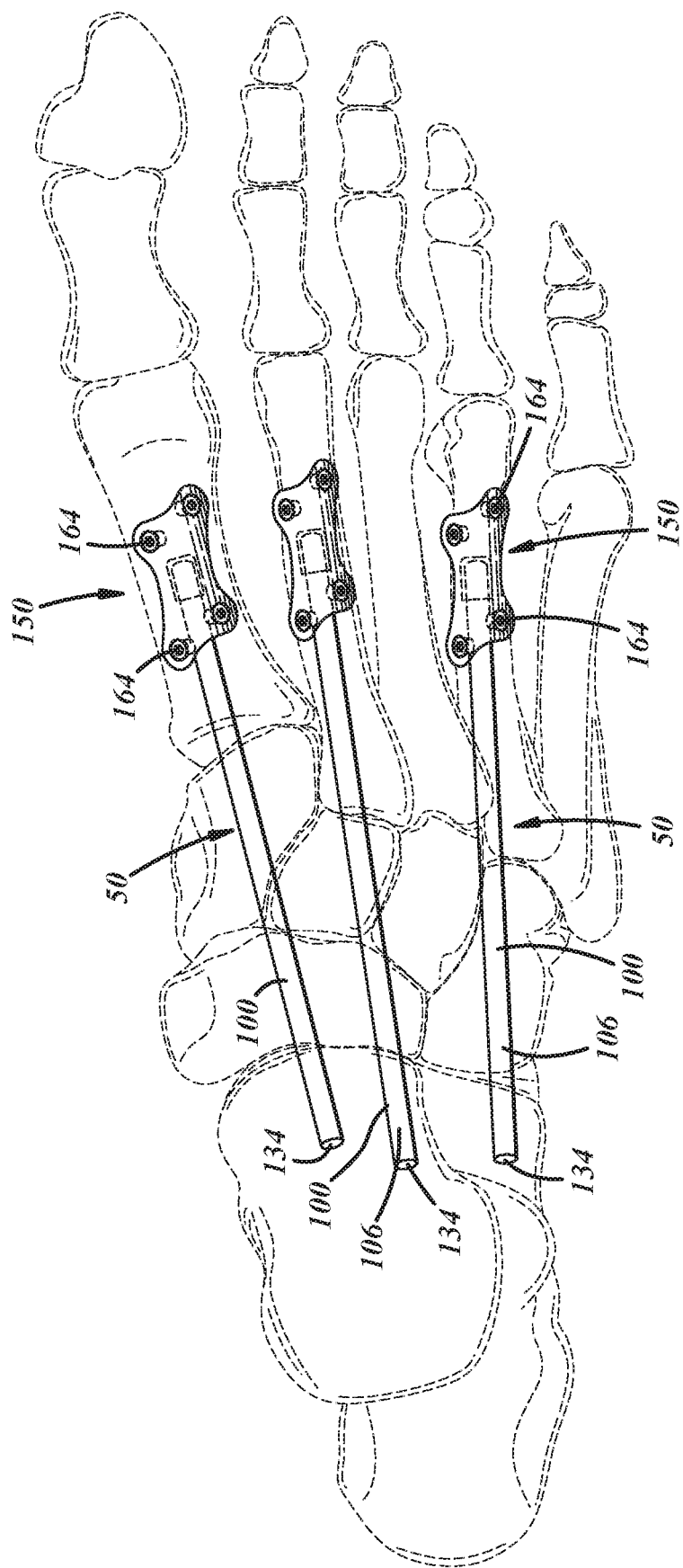
FIG. 13 is a top view depicting a human foot with several assembled rod-plate constructs of the internal fixation system.
Figure 14:
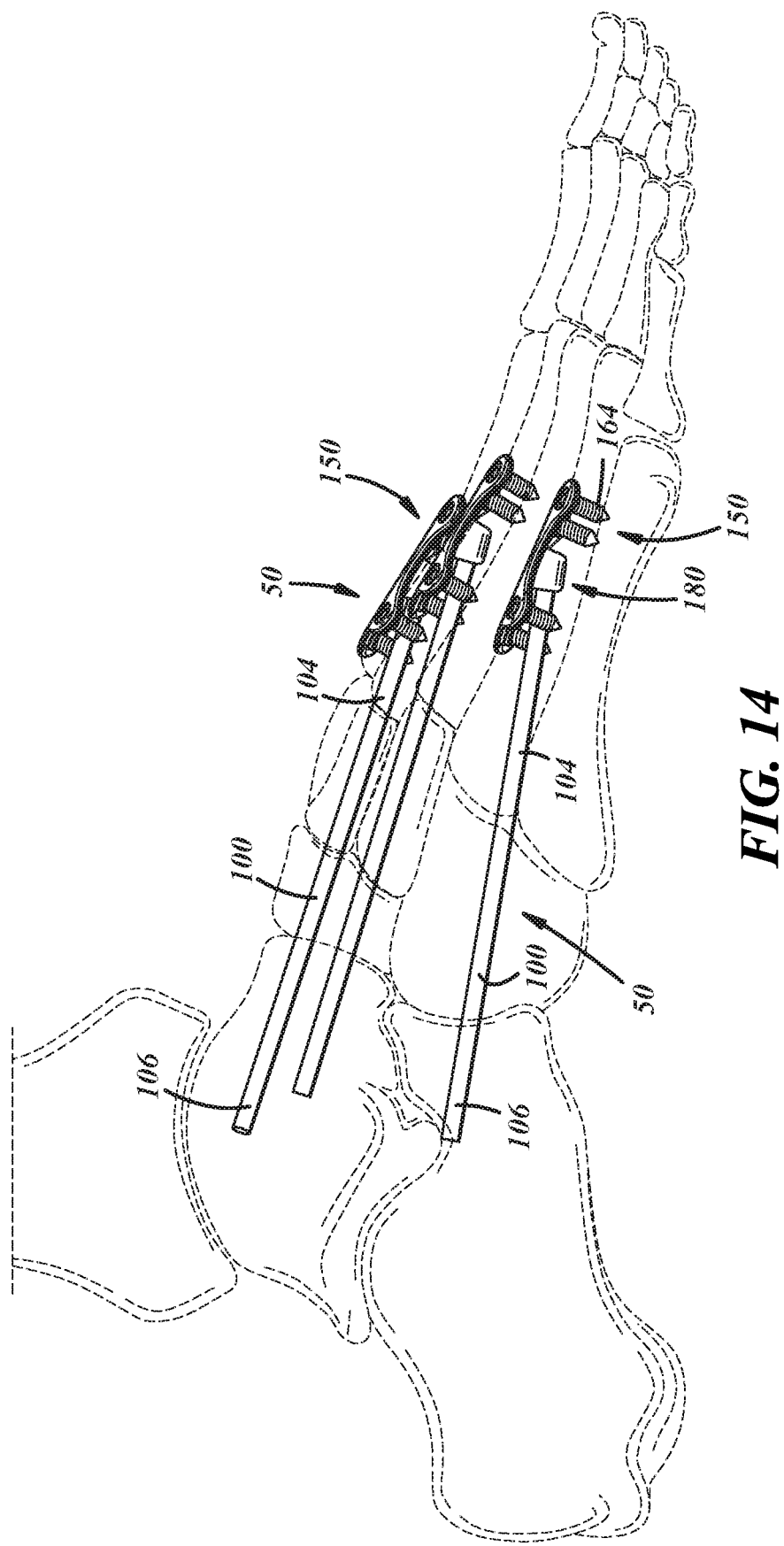
FIG. 14 is a side elevational view of what is shown in FIG. 13.

FIGS. 13 and 14 depict an embodiment of the rod-plate system 50, in this case comprising multiple rod-plate constructs implanted in a human foot. Of course, it is readily recognized that the number of rod-plate constructs needed for a particular patient may be determined by the surgeon.

In use, implantation of a rod-plate construct may begin by first aligning and preparing each of the targeted bones for fusion. An appropriately sized opening into the medullary canal of a targeted metatarsal is made on its dorsal aspect at its midportion. A guidewire is then passed through the opening, through the medullary canal, and continues through the other bones to be fused. Optionally, the guidewire may be passed through to the talus or calcaneus. An appropriately-sized cannulated drill is then passed over the guidewire and used to create a passage within the bones to receive rod 100.

Rod 100, having the selected and corresponding length to that of the drilled passage, is connected to plate 150. The second end 106 of rod 100 is then inserted into the opening and through the passage until projection 180 of plate 150 comes to rest within the dorsal aspect opening in the metatarsal. Optionally, plate 150 may be shaped to conform to the topography of the metatarsal after insertion, or beforehand. In other embodiments, a rigid pre-contoured plate 150 may be used. Once the rod-plate construct is in place, fasteners, such as screws 164, are then used to fixedly connect plate 150 to the metatarsal.

FIGS. 15-17A depict an exemplary embodiment of shaft system 60 which is a subsystem of internal fixation system 40. Shaft system 60 may be used independently, or in conjunction with other systems, to facilitate the alignment, reduction and fixation of bones.

The prominent component of shaft system 60 is shaft 200. Shaft 200 may be a unitary device, or a modular one comprised of various segments that may be joined together, thus enabling customization of shaft 200. With specific reference to FIG. 15, shaft 200 is modular, and is comprised of segments referred to as cap 202, intermediate spacer 204a, intermediate spacer 204b, and base 206. These segments may each be joined to each other at a connection 203 (shown joined in FIGS. 16-17A). Connection 203 may be a threaded connection, a Morse-taper type connection, or any other suitable connection known in the art. It is further understood that one or more different types of connections 203 may be used to assemble shaft 200.

Cap 202 is a hollow body comprising a bore 215. Cap 202 further comprises a first end 210 having a rounded terminal portion 214 which facilitates shaft 200's insertion into bone during implantation, and a second end 212 where bore 215 has internal threads 216 to enable cap 202 to be connected to another mateable segment of shaft 200. Cap 202 further has a transverse through-hole 218 to receive fixation element 220 (FIG. 16) to fix cap 202, and thereby facilitate fixing shaft 200, to bone. More detail about the optional configurations and uses of through-hole 218 will be discussed in more detail later with reference to base 206.

Intermediate spacers 204a and 204b each have similar configurations with the difference being that spacer 204a includes through-hole 218, while spacer 204b does not have any such through-holes. Both spacers 204a, 204b further have a first end 222, an opposite second end 224, and bore 215 extending therebetween, thereby making them hollow. On first end 222, there is a projection 225 with external threads 226. External threads 226 are configured to mate with internal threads 216, to enable a secure connection 203 therebetween, and thus between any one spacer 204a, 204b and cap 202. As is evident from this description, the intention is to enable the easy interchangeability and interconnectability of different segments.

Base 206 also has a first end 232, an opposite second end 234, and bore 215 extending therebetween, thereby making it hollow. On its first end 232, base 206 has a similar projection 225 with external threads 226 as discussed above with reference to other segments, for purposes of interchangeability. Base 206 is also depicted with through-hole 218 to enable its connection to bone. At its second end 234, base 206 also has a slot 240 therethrough to facilitate bringing two bone segments together, otherwise known as reduction, as will be discussed in more detail below. Lastly, base 206 has internal threads 248 at its second end 234. These internal threads 248 are configured to cooperate with external threads 226 of the various segments, as well as with external threads 256 of plug 208. Notably, internal threads 248 may run deeper into bore 215 of base 206 than comparable internal threads 216 in other segments. This is because internal threads 248 are also configured to receive plug 208.

Plug 208 comprises body 255 with external threads 256 that are similar to external threads 226 on the other segments of shaft 200, again for interchangeability, a compression element 260, and an instrument engagement area 265. The insertion of plug 208 into the second end 234 of base 206, and its movement through bore 215, together with slot 240, and the use of a fastener 242 (FIG. 16), enables reduction, as will be discussed yet further in more detail below.

Figure 17:
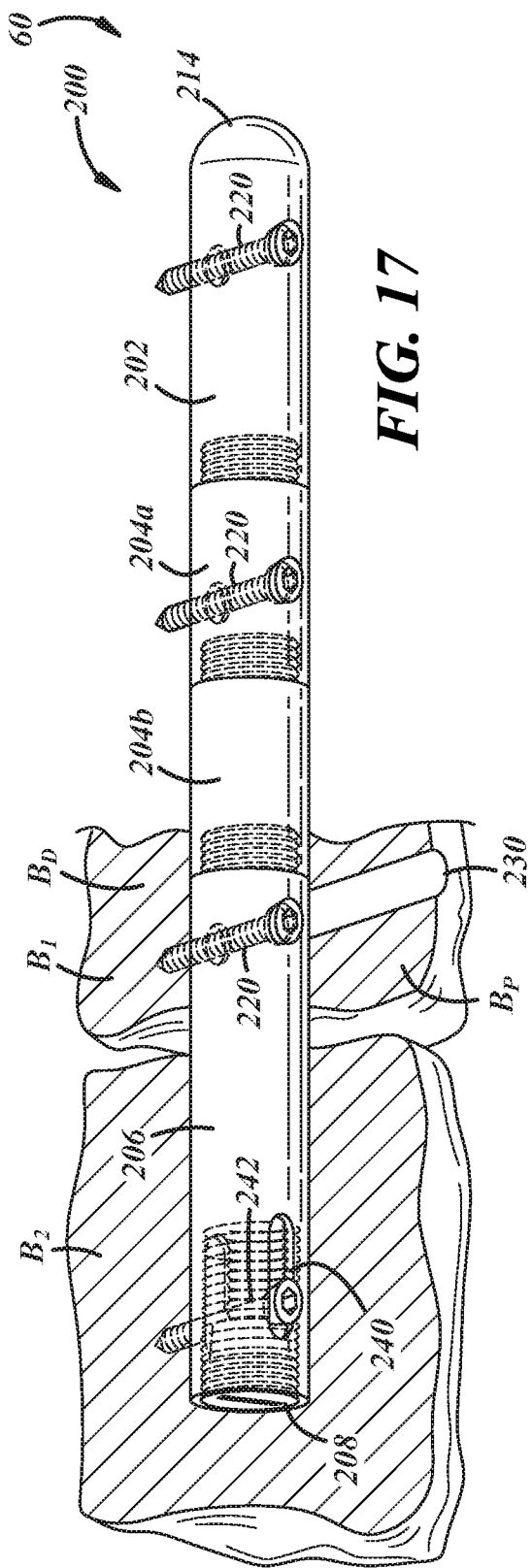
FIG. 17 is a side elevational view of a fully assembled shaft component affixed to two bones prior to reduction.
Figure 17A:
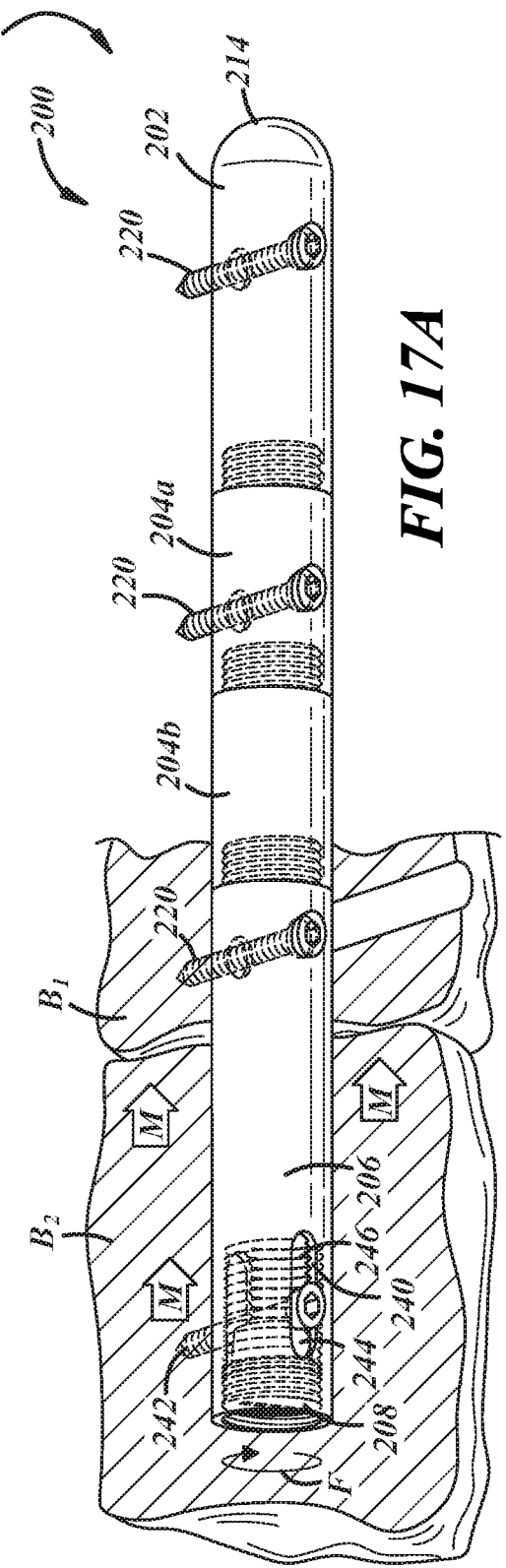
FIG. 17A is a side elevational view of what is shown in FIG. 17, depicting motions that reduce the space between the two bones.

With reference to FIGS. 16-17A, in order to perform reduction, one segment of bone must be stationary, and an adjacent segment of bone must be moved toward the stationary bone segment. In the present embodiment, bone B1 is the stationary bone. Shaft 200 is fixed to bone B1 with screw 220 positioned through through-hole 218 in base 206. Notably, through-hole 218 also provides for further variability of fixation methods of shaft 200 to bone as discussed next.

It is recognized that there are at least two common approaches to fixating shaft 200 in space relative to bone, among various other approaches known in the art. In one such common approach, this is accomplished by fixing proximal bone portion Bp to shaft 200. In the other common approach, this is accomplished by pinning shaft 200 in between two segments of bone.

With reference to the first approach, when shaft 200 is in a bone canal (FIG. 17), a bore 230 is drilled from the proximal bone surface Bp of proximal bone B1 to the exterior of shaft 200. Bore 230 is coaxial with through-hole 218 and sized to allow the head of screw 220 to pass. Screw 220 is then inserted through bore 230 and threaded into a threaded version of through-hole 218. As is evident, and known in the art, it is not necessary for screw 220 to go all the way through base 206, so long as there is sufficient threaded engagement in the first area of contact between screw 220 and base 206. Of course, if more thread engagement is desired, screw 220 may be progressed further to threadably engage base 206 at its second area of contact with base 206. As will be readily recognized, the approach just described from bone surface Bp may be similarly accomplished from the opposite distal bone surface Bd. For this reason, it is desirable to have through-hole 218 fully threaded.

With respect to the second approach of fixating shaft 200 in space relative to bone, the intention is for screw 220 to enter through bore 230, completely extend through shaft 200, and threadably purchase bone portion Bd. While this approach may better call for through-hole 218 to be unthreaded, to increase the variability of usage of shaft 200, the threaded version of through-hole 218 may continue to be employed. Of course, having described the foregoing, it will be readily recognized that various alternatives and permutations of the above configurations of structure and usage may be employed. Additionally, it is noted that through-hole 218 has the same characteristics as through-hole 130 of rod 100.

With further reference to FIGS. 16-17A, in the context of reduction, the bone segment that will be moved toward stationary bone segment B1 is movable bone segment B2. Of course, it is generally recognized that movement is relative. In similar fashion as described for putting screw 220 through through-hole 218 of base 206, a partially threaded screw 242 is put through slot 240, and specifically through slot area 244 which is most distal to base 206's first end 232, and screwed into bone B2. Plug 208 may be introduced into threaded engagement with internal threads 248 of second end 234 of base 206 before or after insertion of screw 242, and positioned at slot area 244. A driver (not shown) is then engaged to plug 208's instrument engagement area 265, and actuated so as to rotate plug 208 in direction F (FIG. 17A), thus translating plug 208 towards slot area 246 by virtue of the translational component of threaded rotation. In so doing, compression element 260 of plug 208 pushes screw 242 linearly along slot 240 from slot area 244 to slot area 246, a distance M. Consequently, this pushes bone segment B2 towards bone segment B1, which is fixedly connected to base 206 via through-hole 218, the same distance M, thus producing reduction.

It will be readily understood by those skilled in the art that the reduction mechanism described above, inclusive of such elements as slot 240 and plug 208, may be positioned on any other one or more segments of shaft 200 for increased variability of the segments of shaft 200. Of course, other means to rotate or otherwise advance plug 208 may be needed in instances where its instrument engagement area 265 is not accessible as in the embodiment described above.

While slot 240 has been described in the context and functionality depicted with reference to shaft 200, a somewhat similar slot 132 is positioned on rod 100 (FIG. 5) as mentioned earlier. The specific mechanism for reduction using slot 132 will be different from that described for slot 240, but such other ways to perform reduction are known in the art. For example, with reference to FIG. 24, if a pin 310 were inserted through slot 132 of rod 100 into one bone, and a screw 220 were inserted through hole 130 of rod 100 into another bone, then a surgeon may manually grip and translate pin 310 and screw 220 toward each other, thereby bringing the two bones together.

The ability to rotationally align one segment of shaft 200 to a desired position relative to another segment of shaft 200, for a variety of purposes, is an engineering function that has many different solutions known in the art. For example, with reference to FIG. 16, it may be desirable to have through-hole 218 on cap 202 oriented 30° in either direction from where it is shown. Similarly, on the same shaft 200, it may be desired for through-hole 218 on spacer 204a to be oriented 15° from where it is shown. One way to accomplish such desired alignment of through-holes 218 in an assembled shaft 200 is to have keyed, timed, or precision threads 216, 226 that enable planned rotational assembly to result in the desired alignment.

The ability to target and insert screws 220, 242 into their respective positions in or through rods 100 and shafts 200 is also an engineering function that has various different solutions known in the art. For example, targeting jigs are known to facilitate the location and identify the orientation of through-holes 218 when shaft 200 is inside bone. Rods 100 and shafts 200 may be configured to cooperate with such targeting jigs.

As was noted earlier with respect to rod 100, shaft 200, and the various other elements described above, may be formed of any suitable material known in the art. For example, shaft 200 may be formed of titanium, or other biocompatible materials having mechanical properties suitable for its contemplated uses. Furthermore, shaft 200 may be coated with any suitable biocompatible coating known in the art, such as hydroxyapatite or the like, or may be uncoated, as needed to suit particular mechanical and clinical needs.

Notably, as will be apparent to those skilled in the art, shafts 200 may be solid rather than hollow, and rods 100 may be hollow rather than solid. Of course, various other adjustments to their respective features may then be made to result in those features maintaining their respective intended functionalities. For example, if shaft 200 were solid rather than hollow, second end 234 of base 206 would still maintain a hollow passageway to enable plug 208 to travel therethrough to effectuate reduction.

Figure 18:
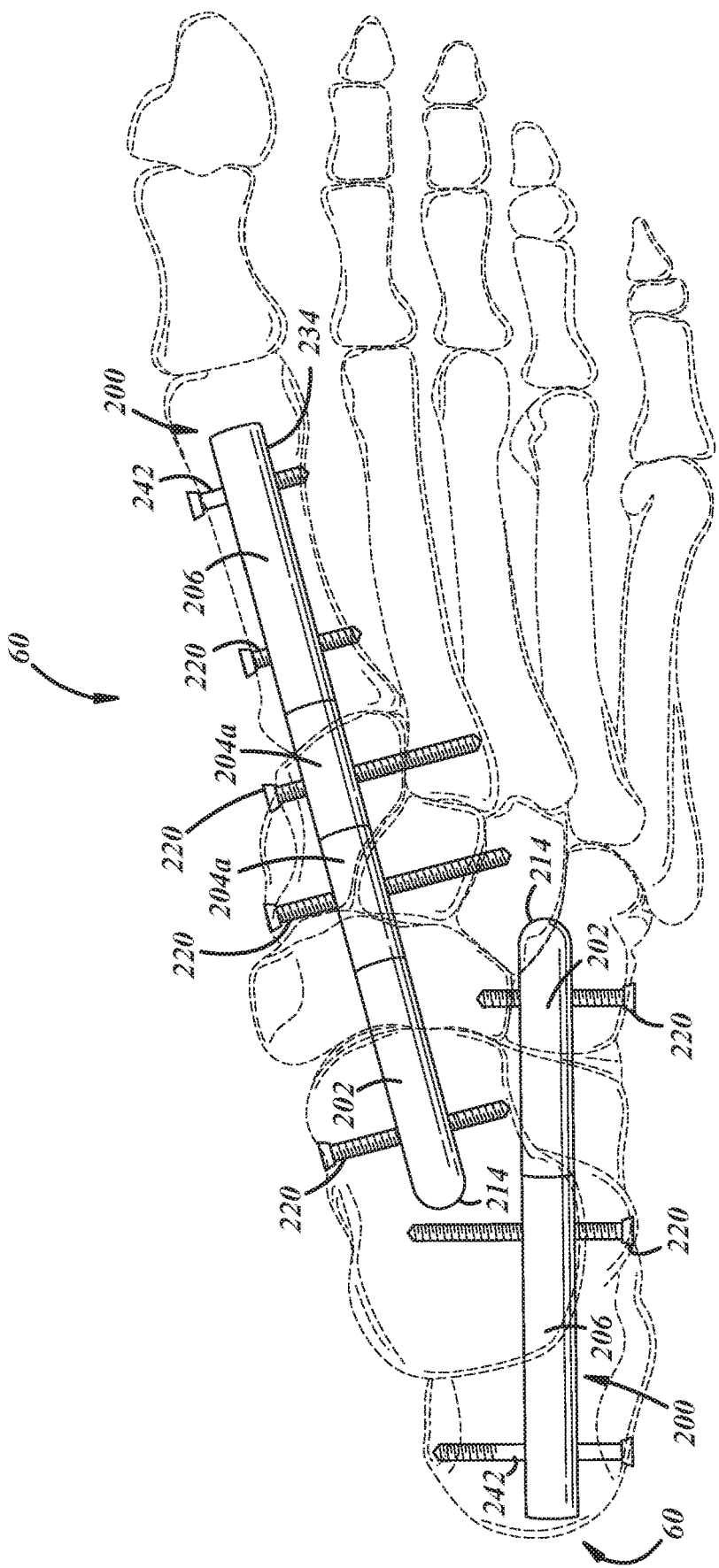
FIG. 18 is a top view of two shafts implanted in a foot.
Figure 19:
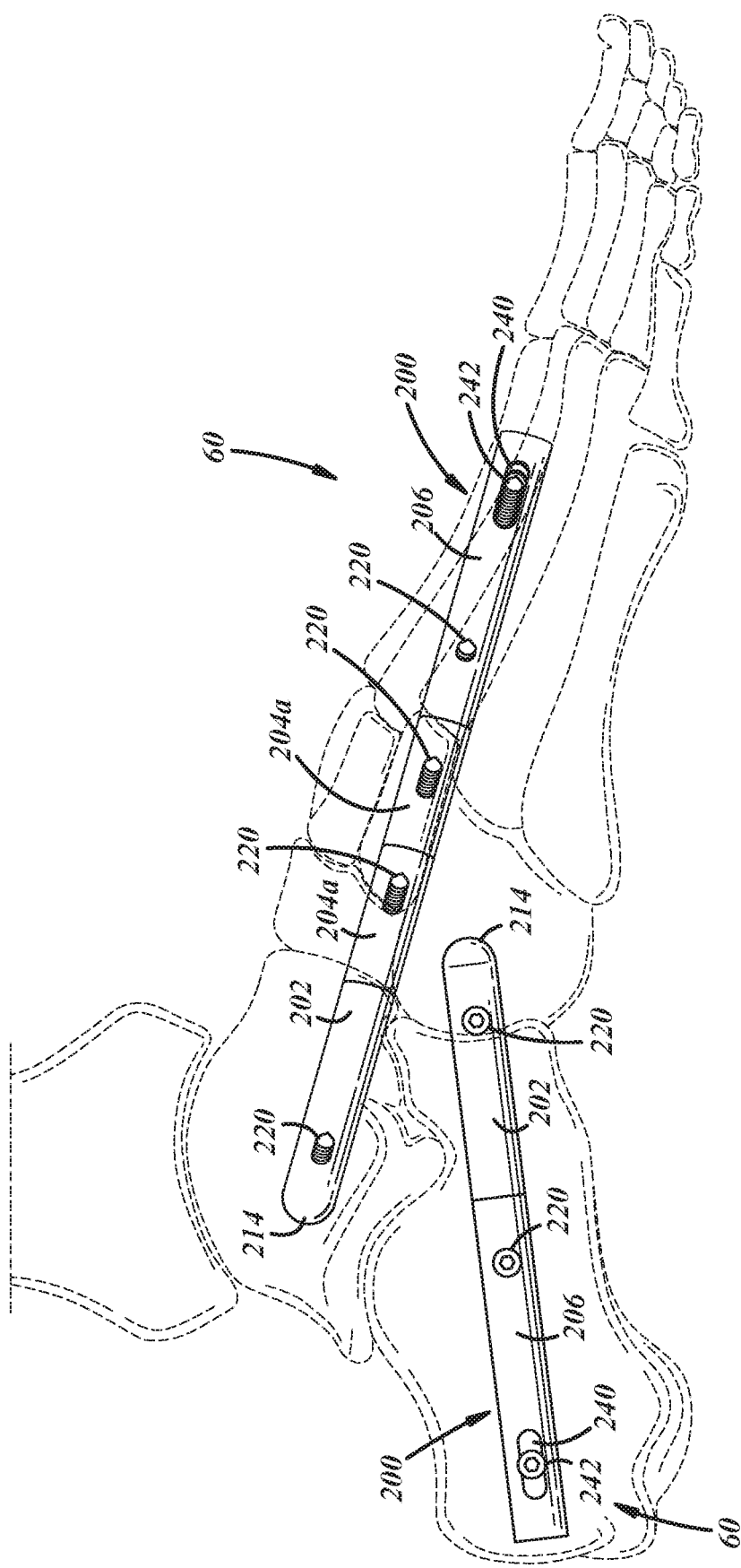
FIG. 19 is a side elevational view of what is shown in FIG. 18.

Referring to FIGS. 18 and 19, two shafts 200 of shaft system 60 are shown implanted in a human foot. The medial shaft 200 is assembled from a cap 202, followed by two spacers 204a, and then a base 206, and is oriented such that base 206 is located in the first metatarsal, and the cap 202 is in the talus. The lateral shaft 200 is assembled from another cap 202 and a base 206. It is oriented such that base 206 is in the calcaneus, and cap 202 is in the cuboid. Each shaft 200 is depicted as fixed in place to bone by various screws 220, 242.

Each of the bones targeted for fusion are first manually aligned and prepared for accepting shaft system 60. For example, to implant the medial shaft 200, the first metatarsal phalangeal joint is exposed via a dorsal incision. A guidewire to direct reaming of the medullary canal is then introduced near the center of the metatarsal head, directed through the metatarsal body, medial cuneiform navicular, and into the talar neck. Reaming is then conducted iteratively over the guidewire until a canal having an appropriate internal diameter to receive shaft 200 is formed through the bones. Of course, it is recognized that various anatomical landmarks and sizes of bones will ultimately determine the selection of the diameter and length of the canal, and therefore the diameter and length of shaft 200 to be used in it, as well as which segments of shaft 200 should be selected and the order in which they should be assembled.

Prior to insertion of shaft 200, it may be connected to a targeting jig (not shown). The targeting jig projects the positions of the relevant through-holes on shaft 200, such as holes 218, and thus enables a surgeon to accurately place screws 220 through the targeting jig directly into or through each targeted hole 218, for example, as the case may be, after shaft 200 is placed in the reamed bone canal.

Once the targeting jig is attached to the medial shaft 200, medial shaft 200 is then inserted into the reamed bone canal. A screw 220 is then placed through the jig and through hole 218 of cap 202 which is located in the talus. Then, screw 242 is placed through the jig and through slot 240, which, in such embodiment, is in the first metatarsal. Plug 208, located in second end 234 of base 206 is then rotationally actuated to translate axially along slot 240, thus compressing all the bones between screw 242 and screw 220 along shaft 200, to a desired orientation, at which point, other screws 220 will be inserted through shaft 200 to lock the compressed bones in place relative to shaft 200. Alternatively, some or all of the compression may also be performed by other techniques known in the art.

In light of the foregoing, the preparation of bones, the selection, assembly, and insertion of lateral shaft 200, and the reduction and fixation of the associated bones, will be apparent to those skilled in the art.

With reference to FIGS. 20-21, there is depicted the implanted combination of a rod-plate system 50 and shaft system 60. Specifically, there are two rod-plate constructs, and two shafts 200. Notably, a rod 100 may be connected to a shaft 200, and is depicted as such. This may be accomplished using screw 220, or by other means. As will be apparent to those skilled in the art, any number, combination, and configuration of rod-plate constructs and shafts may be employed, and also connected to each other at different points, as necessary to address various clinical needs.

FIG. 22 depicts a midfoot component in the form of plate 280, having screw holes 281 adapted to receive screws 282 (FIG. 23) that attach plate 280 to bone. Plate 280 is generally known in the art. Plate 280 may be malleable, to enable it to be shaped in situ to conform to target anatomy to which it will be attached, or provided in multiple generic rigid shapes, or otherwise custom manufactured through patient-matching technologies. It is intended to be used on its own, or in combination with one or more systems and subsystems of fixation system 10.

FIG. 23 depicts plate 280 implanted in a foot in combination with rod-plate constructs and shafts 200, wherein certain of the rods 100 and shafts 200 are interconnected. The possibility to combine all these subsystems offers increased variability and flexibility to treat a greater variety of clinical needs.

FIG. 24 depicts an internal fixation subsystem, namely shaft system 60, connected to an external fixation system 80. External fixation system 80 comprises one or more frames 302 each having a plurality of openings 304, a plurality of connectors 306, and pins 310. Pins 310 are depicted as partially threaded on their distal ends, and may also optionally be unthreaded, or fully threaded, as is known in the art. This basic external fixation system 80 is also well known in the art.

Notably, an aspect of the present invention is the connection of external fixation system 80 to the shaft system 60, as depicted in FIG. 24. Specifically, frame 302 is connected using pins 310 inserted through connectors 306 to shafts 200. It is thusly evident that many other configurations, arrangements and connections of external fixation system 80 with one or more of certain subsystems of internal fixation system 40 are possible. For example, external fixation system 80 may be connected to an implanted rod-plate system 50.

The added ability to combine and connect external fixation system 80 with the various subsystems of internal fixation system 40 increases yet further the variability and flexibility of the overall fixation system 10 to treat a yet greater variety of clinical needs.

FIG. 25 depicts a sole component 400 of external fixation system 80. Sole component 400 is intended to be used in conjunction with external fixation system 80 and is meant to provide a weight-bearing platform underneath a patient's foot to enable a patient with fixation system 10 to walk.

Sole 400 comprises a housing 402 adapted to hold a removable liner 404 therein. With reference from front 410 to back 412, housing 402 has a top surface 406, side walls 407 and a bottom surface 408 that spans housing 402 from front 410 to back 412. Bottom surface 408 is the surface that comes in contact with the ground when a patient walks while wearing fixation system 10. As such, its shape, texture and materials may be adapted as known in the art to facilitate safer walking. For example, bottom surface 408 may be made of, or coated with, rubber to increase the coefficient of friction between sole 400 and the ground, thus diminishing the chances of a patient slipping while they walk with fixation system 10. Other embodiments are envisioned to accomplish this goal.

The profile of bottom surface 408 may be a complex series of continuous curves, such as a tighter curve toward the back 412, which may be known as the heel-strike area, eventually transitioning to a gradual curve toward the front 410, over which the forefoot rolls during gait. Of course, other shapes are contemplated.

Liner 404 may include an inflatable air bladder (not specifically shown) and be filled with any appropriate fluid. The bladder may have a valve (not specifically shown) through which air or other fluid may be introduced or evacuated to achieve the optimal density and size to support a particular weight or pressure requirement. Liner 404 may optionally be housed in a fabric shell (not specifically shown). The shell can be moisture wicking and machine washable for easy cleaning and maintenance. The shell may also be removable via a zipper, hook-and-loop fasteners, snaps, and the like.

Sole 400 also has slots 424, enabling it to be connected to frame 302 (FIG. 26), as will be discussed in more detail below. Slots 424 may be formed within the material of housing 402, or may alternatively be solid tubes affixed to either the inside or outside of housing 402, as may be readily understood by those skilled in the art.

FIG. 26 is an exploded view of certain components of external fixation system 80 used to assemble sole 400 to frame 302. More specifically, connectors 306 have threaded openings 307 on their various faces, enabling them to be connected to frame 302 and to other components using bolts 308, thus making them universal.

Struts 426 are used to connect sole 400 to frame 302. Struts 426 have eyelets 428 to enable such a connection. For example, after connectors 306 are connected to frame 302 with bolts 308, eyelets 428 of struts 426 would be aligned with connectors 306, and additional bolts 308 would be put through eyelets 428 and screwed into connectors 306, thus pinning and fixing struts 426 to frame 302. Struts 426 shall also be connected to sole 400 in any variety of ways known to those skilled in the art. For example, struts 426 may be inserted and glued into slots 424.

Struts 426 may be of unitary construction, or alternatively, may be comprised of two or more components enabling strut 426 to expand and compress as well as be fixed in place at a desired length. Struts 426 may also be made from various materials, from stiff metals, to more elastomeric materials that may further facilitate absorption of striking forces during gait.

Having thus described the invention in detail, it is to be understood that the foregoing description is not intended to limit the spirit or scope thereof. It will be understood that the embodiments of the present disclosure described herein are merely exemplary and that a person skilled in the art may make any variations and modification without departing from the spirit and scope of the disclosure. All such variations and modifications, including those discussed above, are intended to be included within the scope of the disclosure.

What is claimed is:

1. A fixation system for immobilizing a skeletal structure, comprising:
   an internal fixation system comprising one or more of
     a rod-plate system, and
     a shaft system; and
   an external fixation system;
   wherein the rod-plate system comprises
     a rod affixed directly to a plate, the rod being adapted to be positioned in a bone canal, the rod further being modularly comprised of multiple segments each joinable by a connection, and the plate being adapted to be positioned on bone near the bone canal;
   wherein the shaft system comprises a shaft with a longitudinal axis, a slot on the shaft oriented in the direction of the longitudinal axis, and a hole on the shaft oriented at an angle to the longitudinal axis, the shaft further adapted to be positioned in a bone canal and configured to move two bone segments that comprise the bone canal toward each other; and wherein the external fixation system comprises a frame connected to a sole, the sole having a bottom adapted to contact ground.

2. The fixation system of claim 1, wherein the external fixation system further comprises a pin, and the external fixation system is connected to the rod-plate system or the shaft system via the pin, and the rod-plate system or the shaft system is located in bone.

3. The fixation system of claim 1, wherein the rod-plate system is connected to the shaft system when both systems are located in bone.

4. The fixation system of claim 3, further comprising a midfoot plate system attached to bone, the midfoot plate system comprising a plate and a fastener.

5. The fixation system of claim 1, wherein the connection of the multiple segments of the rod of the rod-plate system is a threaded connection or a Morse-taper connection.

6. The fixation system of claim 1, wherein the plate of the rod-plate system comprises a first side adapted to face bone, an opposite second side, a length, a width, a plate axis along the length, and a projection extending from the first side.

7. The fixation system of claim 6, wherein the projection includes an opening to communicate with the rod of the rod-plate system.

8. The fixation system of claim 7, wherein the opening in the projection communicates with the rod via a threaded connection.

9. The fixation system of claim 7, wherein the opening is cylindrical and has a longitudinal opening axis, and the opening is oriented such that the opening axis is at an angle to the plate axis.

10. The fixation system of claim 1, wherein the shaft of the shaft system is modularly comprised of multiple segments each joinable by a connection.

11. A fixation system for immobilizing a skeletal structure, comprising:
    an internal fixation system having
        a rod-plate system, and
        a shaft system; and
    an external fixation system;
    wherein the rod-plate system comprises
        a rod affixed to a plate without a separate connecting member therebetween, the rod being adapted to be positioned in a bone canal, the rod further being modularly comprised of multiple segments each joinable by a connection, and
        the plate being adapted to be positioned on bone near the bone canal,
    the plate further having a first side adapted to face bone, an opposite second side, a length, a width, a plate axis along the length, and a projection extending from the first side, the projection having a cylindrical opening with a longitudinal opening axis, and the opening being oriented such that the opening axis is at an angle to the plate axis;
    wherein the rod-plate system is connected to the shaft system with a fixation element when both systems are located in bone; and
    wherein the external fixation system is connected to one of the rod-plate system or shaft system.

12. The fixation system of claim 11, wherein the connection of the multiple segments of the rod of the rod-plate system is either a threaded connection or a Morse-taper connection.

13. The fixation system of claim 11, wherein the external fixation system further comprises a pin, and wherein the pin connects the external fixation system to one of the rod-plate system or shaft system.

14. The fixation system of claim 13, wherein the external fixation system further comprises a frame connected to a sole, the sole having a bottom adapted to contact ground.

15. The fixation system of claim 11, further comprising a midfoot plate system attached to bone, the midfoot plate system comprising a plate and a fastener.

* * * * *